US012751773B2

(12) United States Patent
Dos Santos Raposo et al.

(10) Patent No.: US 12,751,773 B2
(45) Date of Patent: Oct. 6, 2026

(54) METHODS AND SYSTEMS FOR CALIBRATING SURGICAL INSTRUMENTS FOR SURGICAL NAVIGATION GUIDANCE

(71) Applicants: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(72) Inventors: Carolina Dos Santos Raposo, Coimbra (PT); João Pedro De Almeida Barreto, Coimbra (PT); Nicholas R. Labriola, Westborough, MA (US); Diogo Emanuel Ribas Vaz, Corvo (PT)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 243 days.

(21) Appl. No.: 18/777,812

(22) Filed: Jul. 19, 2024

(65) Prior Publication Data

US 2025/0143799 A1 May 8, 2025

Related U.S. Application Data

(60) Provisional application No. 63/597,002, filed on Nov. 8, 2023.

(51) Int. Cl.
*A61B 34/20* (2016.01)
*A61B 90/00* (2016.01)

(52) U.S. Cl.
CPC ........ *A61B 34/20* (2016.02); *A61B 2090/363* (2016.02)

(58) Field of Classification Search
CPC .............. A61B 2090/363; A61B 34/20; A61B 2034/2046–2074
USPC .......................................................... 600/424
See application file for complete search history.

(56) References Cited

U.S. PATENT DOCUMENTS

| | | | | |
|---|---|---|---|---|
| 7,831,082 | B2 * | 11/2010 | Holsing | A61B 90/36 382/128 |
| 8,190,389 | B2 | 5/2012 | Kim et al. | |
| 10,499,996 | B2 * | 12/2019 | de Almeida Barreto | A61B 34/10 |
| 10,675,116 | B2 * | 6/2020 | Olive | A61B 90/39 |
| 11,065,064 | B2 * | 7/2021 | Pinsky | A61B 5/062 |
| 2017/0238996 | A1 * | 8/2017 | Frame | A61B 34/20 |
| 2019/0192230 | A1 * | 6/2019 | Siemionow | A61B 34/20 |
| 2020/0129241 | A1 | 4/2020 | Forstein et al. | |
| 2022/0156569 | A1 | 5/2022 | Shin et al. | |

(Continued)

OTHER PUBLICATIONS

Bo, Sun, et al., "Surgical instrument recognition and calibration for optical tracking system", IEEE International Conference on Robotics and Biomimetics, Dec. 2010, pp. 1376-1381.

(Continued)

*Primary Examiner* — Matthew J Lawson
(74) *Attorney, Agent, or Firm* — Dickinson Wright PLLC

(57) ABSTRACT

Some examples are directed to methods, systems, and related tools for calibrating a unique fiducial to a surgical instrument with which it is to be physically associated or on which it is to be marked.

18 Claims, 17 Drawing Sheets

(56) References Cited

U.S. PATENT DOCUMENTS

| | | | | |
|---|---|---|---|---|
| 2025/0359944 | A1 * | 11/2025 | Becher | A61B 34/20 |
| 2026/0069375 | A1 * | 3/2026 | Torrie | A61B 90/39 |

OTHER PUBLICATIONS

Wu, Po-Chen, et al., "DodecaPen: Accurate 6DoF Tracking of a Passive Stylus", Proceedings of the ACM Symposium on User Interface Software and Technology (UIST), Oct. 2017, 11 pages.

* cited by examiner

METHODS AND SYSTEMS FOR CALIBRATING SURGICAL INSTRUMENTS FOR SURGICAL NAVIGATION GUIDANCE

CROSS-REFERENCE TO RELATED APPLICATIONS

This application claims the benefit of U.S. Prov. App. No. 63/597,002 filed Nov. 8, 2023 and titled "Methods and Systems to Instrument and Calibrate Surgical Tools With and Without Moving Parts for Video-Based Surgical Navigation." The provisional application is incorporated by reference herein as if reproduced in full below.

BACKGROUND

Surgical procedures in sports medicine typically involve repairs to injured articular tissue and/or bone, and may involve the insertion of implants such as grafts, anchors, and/or other devices.

For example, injury to the anterior cruciate ligament (ACL), which serves as the primary mechanical restraint in the knee to resist anterior translation of the tibia relative to the femur, may be treated with a reconstruction of the ACL. Reconstruction may consist of placement of a substitute graft (e.g., autograft from either the central third of the patellar tendon or the hamstring tendons). The ends of the graft may be placed into respective tunnels prepared through the femur and the tibia and these ends may be attached using interference screws or a suspensory fixation device.

As with other kinds of surgical procedures, to facilitate good patient outcomes and surgical room operational efficiency, it can be desirable for surgical procedures in sports medicine to be minimally invasive. For example, rather than conducting an ACL reconstruction by making one or more large incisions to completely expose a surgical site to the direct view of a surgeon, it is common for the surgeon to make one or more small incisions—known as working portals—that are just large enough to enable insertion, from outside of the patient through to the surgical site, of distal ends of instruments to be used by the surgeon. The surgeon may then conduct the procedure by manipulating proximal ends of the instruments from outside of the patient thereby to cause the distal ends of the instruments to operate within the surgical site. Once the procedure inside the joint is completed, the instruments may be withdrawn, and the working portals closed. Due to their small size, the working portals once closed may tend to heal quickly and with little complication.

In a minimally invasive procedure known as arthroscopic surgery, the surgeon may be guided by what is captured within the field of view of an endoscope inserted through a working portal into the surgical site. The procedure may be computer-assisted in the sense that a controller is used for arthroscopic navigation within the surgical site. The controller may provide computer-assistance by tracking locations of various objects within the surgical site, such as the location of a bone and various instruments within an internal frame defined by the three-dimensional coordinate space of the view of the endoscope. Examples of methods and systems for such internal surgical navigation, including for internal video-based surgical navigation, are described in U.S. Pat. No. RE49930E1 to Barreto ("Barreto 1"), and certain aspects are described in PCT Publication No. WO/2023/034194 to Quist et al. ("Quist").

Within the surgical site, a bone fiducial may be affixed to the bone of the patient thereby to establish a coordinate system (or "frame") for the surgical site. An instrument fiducial may be physically associated with or integral to a surgical instrument to be used during a surgical procedure. The instrument fiducial itself may be calibrated to the surgical instrument such that various geometric entities of the field instrument (such as, in the case of a tibial aimer, its tip and the axis of its barrel or, in the case of a pointer probe, its tip) have a known pose (i.e., position and orientation) with respect to the instrument fiducial (i.e. in the frame of the instrument fiducial). In this way, when the instrument fiducial is captured within the field of view of an endoscope inserted through a working portal into the surgical site, video images captured by the endoscope may be processed to determine the pose of the instrument fiducial and, in turn, the poses of the geometric entities. Furthermore, the poses of these geometric entities may be determined with respect to the frame of the surgical site to which a bone model has been registered. This may be done by, when both the bone fiducial and the instrument fiducial are captured within the field of view of the endoscope, processing the video images and calculating a transform between the frame of the surgical instrument as established by the instrument fiducial and the frame of the surgical site as established by the bone fiducial. By having the poses of the geometric entities of the surgical instrument in the frame of the surgical site, a surgeon can be provided with computer-based guidance during arthroscopic surgery as to positioning and placement of the surgical instrument itself with respect to the surgical site.

Manufacturing of surgical instruments themselves can be done with very low error tolerances using, for example, a CNC (Computer Numerical Control) machine. Because of this, one copy of a surgical instrument manufactured according to a digital model such as a CAD (Computer Aided Design) model can be made almost identical to every other copy of the surgical instrument that is manufactured according to that digital model. On the other hand, manufacturing and marking of instrument fiducials to provide visual patterns discernable for video-based navigation using processes such as printing, inking, engraving, laser marking, or anodization tend to be done with high error tolerances. Because a given copy of an instrument fiducial created using such processes can vary substantially from other copies of the instrument fiducial, each instrument fiducial that is created to be affixed to or otherwise applied to a surgical instrument must be calibrated to the surgical instrument itself on a per-instance basis. Such a calibration may specify the pose of each geometric entity of the surgical instrument in the frame of the instrument fiducial, so that during a surgical procedure a data file encoding the calibration can be retrieved and used by a video-based surgical navigation system to determine the poses of the geometric entities of the instrument in the frame of the surgical site.

Calibration can be somewhat time-consuming and laborious. It can be useful to ensure that calibration is not required to be done by a surgeon during a surgical procedure. It is indeed possible to manufacture a surgical instrument, to affix or otherwise apply an instrument fiducial to the surgical instrument, and to calibrate the instrument fiducial to the surgical instrument, as part of an overall manufacturing-assembly-calibration process conducted prior to delivery of the product to a surgeon. Accordingly, a surgeon may simply take delivery of a prepared, sterilized and calibrated surgical instrument. The surgeon may then ensure the surgical controller is aware of the particular calibration that had been done for that surgical instrument to its fiducial, and thereafter proceed with the other steps of the surgical procedure with the benefits of video-based surgical navigation.

Where it is desirable to re-use a particular surgical instrument for more than one surgical procedure, the surgical instrument must be sterilized between the procedures. However, a sterilization process, such as one using an autoclave, can tend to degrade the visual pattern of a fiducial on a surgical instrument. Degradation of the visual pattern may reduce the track-ability of the fiducial during the next and any subsequent surgical procedures. Some fiducials, therefore, cannot practically be reused. However, it would be useful to provide surgical instruments that themselves can be used repeatedly with sterilization between uses, and that can be tracked using video-based surgical navigation, without also requiring calibration of newly-applied fiducials to be done at the time of the surgical procedure.

SUMMARY

Disclosed herein are methods and systems for calibrating a unique fiducial that is to be physically associated with a surgical instrument to be used for a surgical procedure (a "field instrument"), by calibrating the unique fiducial to a digital model of the field instrument. By calibrating the unique fiducial to a digital model of the field instrument, the poses of geometric elements of the digital model may be determined with respect to the unique fiducial. The unique fiducial may thereafter be delivered to a surgical site and simply physically associated with the field instrument without further calibration, providing a video-based surgical navigation system with the correct poses of the geometric elements with respect to the surgical site. Because of the low error tolerances in the manufacturing of the field instrument itself, the calibration of the unique fiducial to the digital model of the field instrument may serve as a calibration of that unique fiducial to each actual field instrument manufactured according to the digital model. Because the actual field instrument with which the unique fiducial will eventually be physically associated does not have to be present for the calibration of a unique fiducial, the field instrument can be sterilized and used repeatedly, and simply physically associated with an already-calibrated replacement unique fiducial for each successive surgical procedure.

For implementations in which the field instrument itself may be printed/engraved or otherwise directly marked with visual markings that serve as a fiducial, the field instrument may not be reliably trackable after a sterilization. However, disclosed herein are methods and systems for using a calibration jig for calibration of directly-marked field instruments, proposed herein with the aim of simplifying, and reducing the time required for, the calibrations of single-use field instruments.

Furthermore, provided herein are methods for configuring a surgical controller to determine poses of geometric entities by retrieving stored geometric entity data for a unique fiducial to be physically associated with a field instrument.

One example is a method of generating, for a unique fiducial, geometric entity data corresponding to a field instrument, the method comprising: physically associating the unique fiducial with a calibration instrument; generating a first transformation from a frame M of a digital model of the field instrument to a frame O of the unique fiducial using the calibration instrument; calculating based on the first transformation, for each of at least one geometric entity of the digital model in the frame M, at least one pose of the geometric entity in the frame O; and electronically storing, in association with an identification of the unique fiducial, each of the at least one pose as the geometric entity data, wherein the unique fiducial is physically dissociated from the calibration instrument to be physically associated with the field instrument for use in a video-based surgical navigation.

In the example method, generating the first transformation may comprise registering each of a plurality of locations along the digital model of the field instrument to a counterpart location along the calibration instrument.

In the example method, a calibration fiducial may be physically associated with the calibration instrument and a first intermediate transformation from the frame M to a frame O' of the calibration fiducial may have been generated using the calibration instrument, and in the example method generating the first transformation may comprise: generating a second intermediate transformation from the frame O' to the frame O, wherein the first transformation is a combination of the first intermediate transformation and the second intermediate transformation.

In the example method, generating the second intermediate transformation from the frame O' to the frame O may comprise: capturing at least one digital image containing both the unique fiducial and the calibration fiducial; and processing the at least one digital image to generate the second intermediate transformation.

In the example method, the field instrument may be configured to assume multiple physical states, and in the example method the calculating may comprise: calculating based on the first transformation, for at least one of the at least one geometric entity of the digital model in the frame M, poses of the geometric entity in the frame O, wherein each of the poses corresponds to a respective one of the physical states.

In the example method, the field instrument may be a tibial aimer having an aimer arm and a handle, and the physical states may be positions of the aimer arm with respect to the handle.

In the example method, the geometric entity data may define, for a line representing an axis of a bullet of the tibial aimer, multiple poses of the line with respect to the unique fiducial, each of the poses of the line corresponding to a respective position of the aimer arm with respect to the handle.

In the example method, the geometric entity data may define a point representing a location of a tip of the aimer arm.

Another example is a method of generating geometric entity data for a field instrument having a unique fiducial, the method comprising: physically associating a calibration instrument having a first calibration fiducial with a calibration jig having a second calibration fiducial; generating a first transformation from a frame L of the calibration instrument to a frame M of the calibration jig using the first calibration fiducial and the second calibration fiducial; calculating based on the first transformation, for each of at least one geometric entity of the calibration instrument in the frame L, at least one pose of the geometric entity in the frame M; physically dissociating the calibration instrument from the calibration jig; physically associating the field instrument or a component thereof with the calibration jig; generating a second transformation from the frame M of the calibration jig to a frame N of the field instrument using the second calibration fiducial and the unique fiducial; calculating based on the second transformation, for each pose of the at least one geometric entity in the frame M, at least one counterpart pose of the geometric entity in the frame N; and electronically storing, in association with an identification of the unique fiducial, each counterpart pose as the geometric entity data, wherein the field instrument or the component thereof is physically dissociated from the calibration jig for use in a video-based surgical navigation.

In the example method, the field instrument may be configured to assume multiple physical states, and in the example method the calculating based on the first transformation may comprise calculating, for at least one of the at least one geometric entity of the calibration instrument in the frame L, poses of the geometric entity in the frame M, wherein each of the poses corresponds to a respective one of the physical states, and in the example method the calculating based on the second transformation may comprise calculating, for the poses of the geometric entity in the frame M, counterpart poses of the geometric entity in the frame N.

In the example method, the field instrument may be a tibial aimer having an aimer arm and a handle, and the physical states may be positions of the aimer arm with respect to the handle.

In the example method, the geometric entity data may define, for a line representing an axis of a bullet of the tibial aimer, multiple poses of the line with respect to the unique fiducial, each of the poses of the line corresponding to a respective position of the aimer arm with respect to the handle.

In the example method, the geometric entity data may defines a point representing a location of a tip of the aimer arm.

Another example is a method of generating geometric entity data for a field instrument having a unique fiducial, the method comprising: generating a first transformation from a frame L of a digital model of the field instrument to a frame M of a calibration jig using a calibration fiducial of the calibration jig; calculating based on the first transformation, for each of at least one geometric entity of the digital model in the frame L, at least one pose of the geometric entity in the frame M; physically associating the field instrument or a component thereof with the calibration jig; generating a second transformation from the frame M of the calibration jig to a frame N of the field instrument using the calibration fiducial and the unique fiducial; calculating based on the second transformation, for each pose of the at least one geometric entity in the frame M, at least one counterpart pose of the geometric entity in the frame N; and electronically storing, in association with an identification of the unique fiducial, each counterpart pose as the geometric entity data, wherein the field instrument or the component thereof is physically dissociated from the calibration jig for use in a video-based surgical navigation.

In the example method, the field instrument may be configured to assume multiple physical states, wherein the calculating based on the first transformation may comprise calculating, for at least one of the at least one geometric entity of the digital model in the frame L, poses of the geometric entity in the frame M, wherein each of the poses may correspond to a respective one of the physical states, and wherein the calculating based on the second transformation may comprise calculating, for the poses of the geometric entity in the frame M, counterpart poses of the geometric entity in the frame N.

In the example method, the field instrument may be a tibial aimer having an aimer arm and a handle, and the physical states may be positions of the aimer arm with respect to the handle.

In the example method, the geometric entity data may define, for a line representing an axis of a bullet of the tibial aimer, multiple poses of the line with respect to the unique fiducial, each of the poses of the line corresponding to a respective position of the aimer arm with respect to the handle.

In the example method, the geometric entity data defines a point representing a location of a tip of the aimer arm.

Another example is a method conducted by a surgical controller comprising: receiving an identification of an unique fiducial to be physically associated with a field instrument for video-based surgical navigation; retrieving, using the identification, stored geometric entity data that defines, for each of at least one geometric entity corresponding to the field instrument, at least one pose of the geometric entity with respect to the unique fiducial; and while receiving a video stream captured of a surgical site: processing images of the video stream to detect, and determine poses of, the unique fiducial within the surgical site; calculating poses with respect to the surgical site of each of the at least one geometric entity based on the poses of the unique fiducial within the surgical site and the stored geometric entity data; and displaying, on a display device in association with the video stream, surgical navigation information based at least on the poses of the at least one geometric entity with respect to the surgical site.

In the example method, the surgical navigation information may comprise a visual representation of the poses with respect to the surgical site of each of the at least one geometric entity.

In the example method, the surgical navigation information may comprise a visual representation of values calculated based on the poses with respect to the surgical site of each of the at least one geometric entity.

In the example method, the stored geometric entity data may have been generated and stored during a calibration of the unique fiducial to a digital model of the field instrument.

In the example method, the stored geometric entity data may have been generated and stored during a calibration of the unique fiducial to a calibration instrument that physically corresponds to the field instrument.

In the example method, each of the at least one geometric entity is selected from the group consisting of: a point, a line, and a plane.

In the example method, the field instrument may be a tibial aimer, and the at least one geometric entity may comprise: a first geometric entity that is a point to correspond to a location of a tip of the tibial aimer; and a second geometric entity that is a line to correspond to an axis of a bullet of the tibial aimer.

In the example method, the stored geometric entity data may define, for at least one of the at least one geometric entity, multiple poses of the geometric entity with respect to the unique fiducial each corresponding to a respective physical state of the field instrument.

The example method may comprise: receiving an indication of a current physical state of the field instrument; and selecting, from the stored geometric entity data for the calculating, one of the multiple poses of the geometric entity that corresponds to the current physical state.

In the example method, the field instrument may be a tibial aimer having an aimer arm component and a handle component, and wherein each physical state may be a position of the aimer arm component with respect to the handle component.

In the example method, the stored geometric entity data may define, for a line representing an axis of a bullet of the tibial aimer, multiple poses of the line with respect to the unique fiducial, each of the poses of the line corresponding to the position of the aimer arm component with respect to the handle component.

In the example method, the stored geometric entity data may define a point representing a location of a tip of the aimer arm component.

Another example is a surgical controller comprising: processing structure comprising at least one computer processor, the processing structure in communication with a display device; and a memory coupled to the processing structure and storing instructions that, when executed by the processing structure, cause the processing structure to: receive an identification of an unique fiducial to be physically associated with a field instrument for video-based surgical navigation; retrieve, using the identification, stored geometric entity data that defines, for each of at least one geometric entity corresponding to the field instrument, at least one pose of the geometric entity with respect to the unique fiducial; and while receiving a video stream captured of a surgical site: process images of the video stream to detect, and determine poses of, the unique fiducial within the surgical site; calculate poses with respect to the surgical site of each of the at least one geometric entity based on the poses of the unique fiducial within the surgical site and the stored geometric entity data; and display, on the display device in association with the video stream, surgical navigation information based at least on the poses of the at least one geometric entity with respect to the surgical site.

In the example surgical controller, the surgical navigation information may comprise a visual representation of the poses with respect to the surgical site of each of the at least one geometric entity.

In the example surgical controller, the surgical navigation information may comprise a visual representation of values calculated based on the poses with respect to the surgical site of each of the at least one geometric entity.

In the example surgical controller, the stored geometric entity data may have been generated and stored during a calibration of the unique fiducial to a digital model of the field instrument.

In the example surgical controller, the stored geometric entity data may have been generated and stored during a calibration of the unique fiducial to a calibration instrument that physically corresponds to the field instrument.

In the example surgical controller, each of the at least one geometric entity may be selected from the group consisting of: a point, a line, and a plane.

In the example surgical controller, the field instrument may be a tibial aimer, and the at least one geometric entity may comprise: a first geometric entity that is a point to correspond to a location of a tip of the tibial aimer; and a second geometric entity that is a line to correspond to an axis of a bullet of the tibial aimer.

In the example surgical controller, the stored geometric entity data may define, for at least one of the at least one geometric entity, multiple poses of the geometric entity with respect to the unique fiducial each corresponding to a respective physical state of the field instrument.

In the example surgical controller, the instructions may further cause the processing structure to: receive an indication of a current physical state of the field instrument; and select, from the stored geometric entity data to calculate, one of the multiple poses of the geometric entity that corresponds to the current physical state.

In the example surgical controller, the field instrument may be a tibial aimer having an aimer arm component and a handle component, and each physical state may be a position of the aimer arm component with respect to the handle component.

In the example surgical controller, the stored geometric entity data may define, for a line representing an axis of a bullet of the tibial aimer, multiple poses of the line with respect to the unique fiducial, each of the poses of the line corresponding to a respective position of the aimer arm component with respect to the handle component.

In the example surgical controller, the stored geometric entity data may define a point representing a location of a tip of the aimer arm component.

BRIEF DESCRIPTION OF THE DRAWINGS

For a detailed description of example embodiments, reference will now be made to the accompanying drawings in which.

DEFINITIONS

Figure 2:
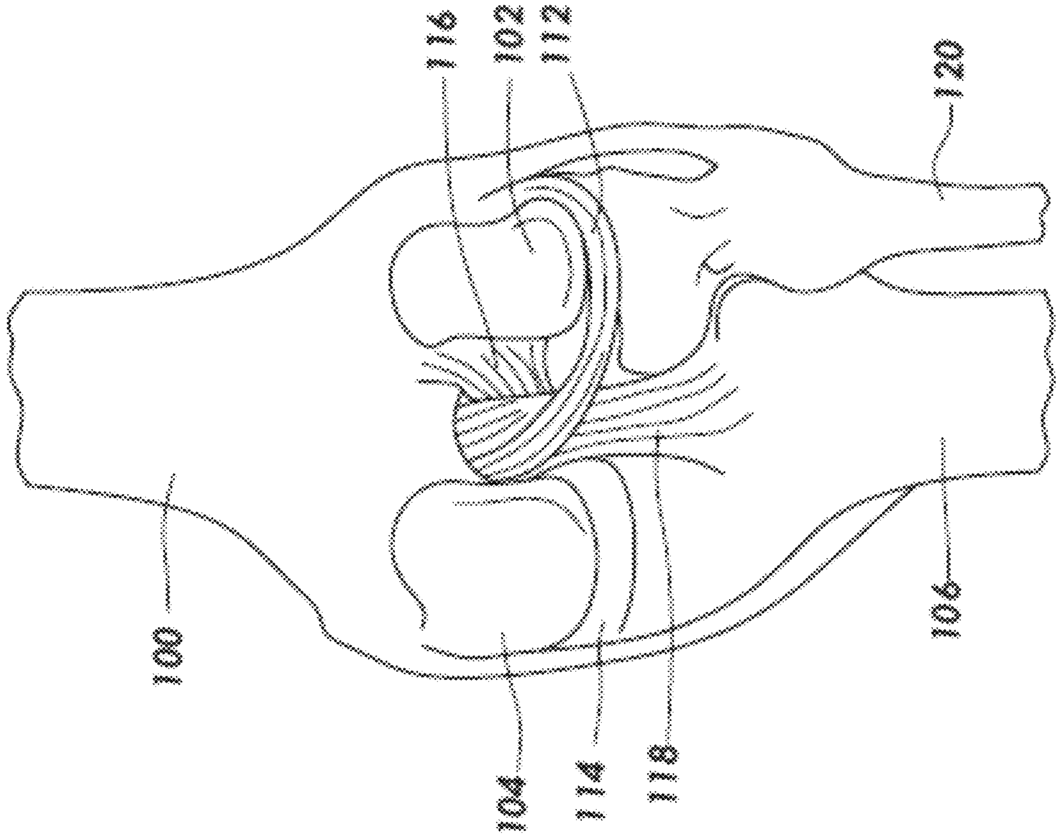
FIG. 2 shows a posterior or back elevation view of the right knee.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Receiving . . . a . . . location" shall mean receiving data indicative of location on a bone within a coordinate space (e.g., a coordinate space of a view of an endoscope). Thus, example systems and methods may "receive . . . a revised-tunnel entry location" being data indicative of a proposed location of a tunnel entry point within a three-dimensional coordinate space. Other example systems and methods may "receive . . . a plurality of locations on a bone" being data indicative locations of an outer surface of a bone as part of registering a bone to a three-dimensional bone model.

An endoscope having "a single optical path" through an endoscope shall mean that the endoscope is not a stereoscopic endoscope having two distinct optical paths separated by an interocular distance at the light collecting end of the endoscope. The fact that an endoscope has two or more optical members (e.g., glass rods, optical fibers) forming a single optical path shall not obviate the status as a single optical path.

"Throughbore" shall mean an aperture or passageway through an underlying device. However, the term "throughbore" shall not be read to imply any method of creation. Thus, a throughbore may be created in any suitable way, such as drilling, boring, laser drilling, or casting.

"Counterbore" shall mean an aperture or passageway into an underlying device. In cases in which the counterbore intersects another aperture (e.g., a throughbore), the counterbore may thus define an internal shoulder. However, the term "counterbore" shall not be read to imply any method of creation. A counterbore may be created in any suitable way, such as drilling, boring, laser drilling, or casting.

"Processing structure" shall mean a single processing device, processor, microprocessing device, microprocessor, computing device, computer, computer system or other device that, like these, can be instructed to and/or configured to conduct computational processing, or an arrangement of multiple processing devices, processors, microprocessing devices, microprocessors, computing devices, computers, computer systems and/or other devices that, like these, can be instructed to and/or configured to conduct computational processing.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various examples are directed to a method of generating, for a unique fiducial, geometric entity data corresponding to a field instrument.

Various examples are directed to a method of generating geometric entity data for a field instrument having a unique fiducial.

Various examples are directed to a method conducted by a surgical controller.

Various examples are directed to a surgical controller.

The discussion below features various examples developed in the context of ACL repair. However, the techniques are applicable to many types of surgical procedures involving an external coordinate system for a surgical room containing a patient and an internal coordinate system of a surgical site within the patient. Such example surgical procedures may include other types of ligament repair, such as medial collateral ligament repair, lateral collateral ligament repair, and posterior cruciate ligament repair. Other examples of surgical procedures may include FAI treatment or other procedures involving resection. Moreover, the various example methods and systems can also be used for planning and placing anchors to reattach soft tissue, such as reattaching the labrum of the hip, the shoulder, or the meniscal root. Furthermore, the various example methods and systems can also be used for planning and navigation of instruments with respect to an anatomy. Thus, the description and developmental context shall not be read as a limitation of the applicability of the teachings. In order to orient the reader, the specification first turns a description of the knee.

Figure 1:
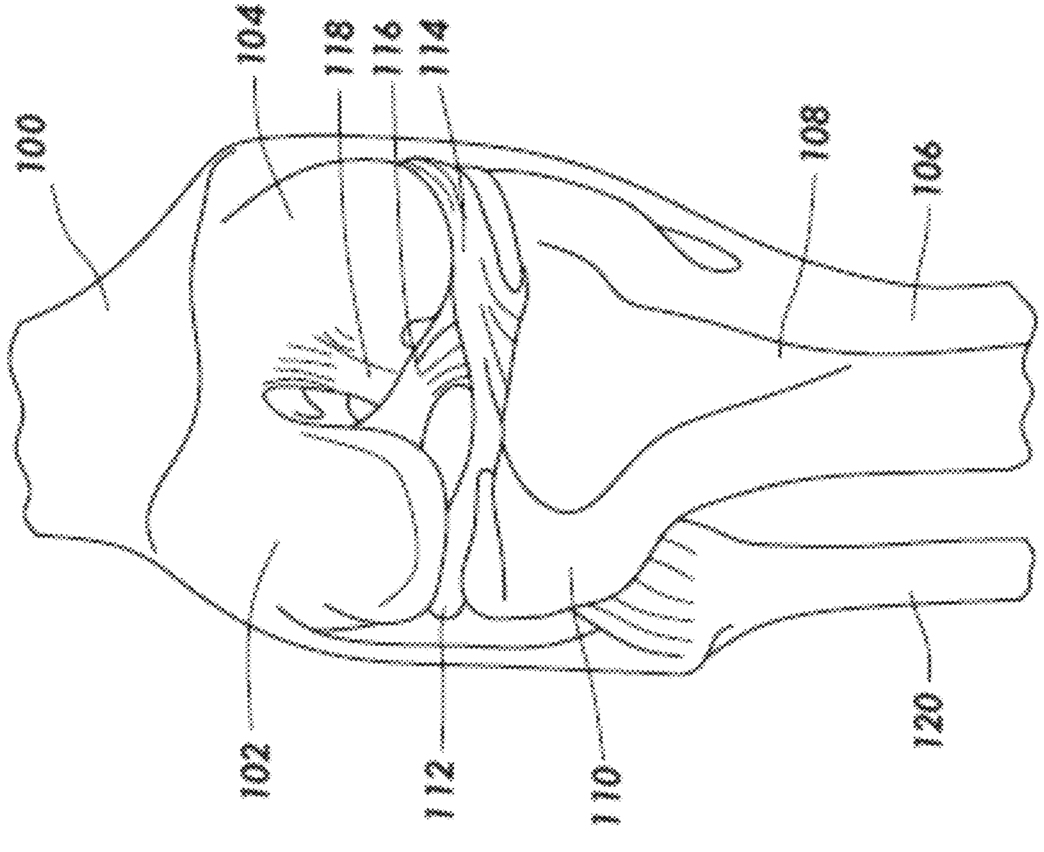
FIG. 1 shows an anterior or front elevation view of right knee, with the patella removed.

FIG. 1 shows an anterior or front elevation view of a right knee, with the patella removed. In particular, visible in FIG. 1 is lower portion of the femur 100 including the outer or lateral condyle 102 and the inner or medial condyle 104. The femur 100 and condyles 102 and 104 are in operational relationship to a tibia 106 including the tibial tuberosity 108 and Gerdy's tubercle 110. Disposed between the femoral condyles 102 and 104 and the tibia 106 are the lateral meniscus 112 and the medial meniscus 114. Several ligaments are also visible in the view of FIG. 1, such as the ACL 116 extending from the lateral side of femoral notch to the medial side of the tibia 106. Oppositely, the posterior cruciate ligament 118 extends from medial side of the femoral notch to the tibia 106. Also visible is the fibula 120, and several additional ligaments that are not specifically numbered.

FIG. 2 shows a posterior or back elevation view of the right knee. In particular, visible in FIG. 2 is lower portion of the femur 100 including the lateral condyle 102 and the medial condyle 104. The femur 100 and femoral condyles 102 and 104 again are in operational relationship to the tibia 106, and disposed between the femoral condyles 102 and 104 and the tibia 106 are the lateral meniscus 112 and the medial meniscus 114. FIG. 2 further shows the ACL 116 extending from the lateral side of femoral notch to the medial side of the tibia 106, though the attachment point to the tibia 106 is not visible. The posterior cruciate ligament 118 extends from medial side of the femoral notch to the tibia 106, though the attachment point to the femur 100 not visible. Again, several additional ligaments are shown that are not specifically numbered.

The most frequent ACL injury is a complete tear of the ligament. Treatment involves reconstruction of the ACL by placement of a substitute graft (e.g., autograft from either the patellar tendon, quad tendon, or the hamstring tendons). The graft is placed into tunnels prepared within the femur 100 and the tibia 106. The current standard of care for ACL repair is to locate the tunnels such that the tunnel entry point for the graft is at the anatomical attachment location of the native ACL. Such tunnel placement at the attachment location of the native ACL attempts to recreate original knee kinematics. In arthroscopic surgery, the location of the tunnel through the tibia 106 is relatively easy to reach, particularly when the knee is bent or in flexion. However, the tunnel through the femur 100 resides within the intercondylar notch. Depending upon the physical size of the patient and the surgeon's selection for location of the port through the skin, and through which the various instruments are inserted into the knee, it may be difficult to reach the attachment location of the native ACL to the femur 100.

Figure 3:
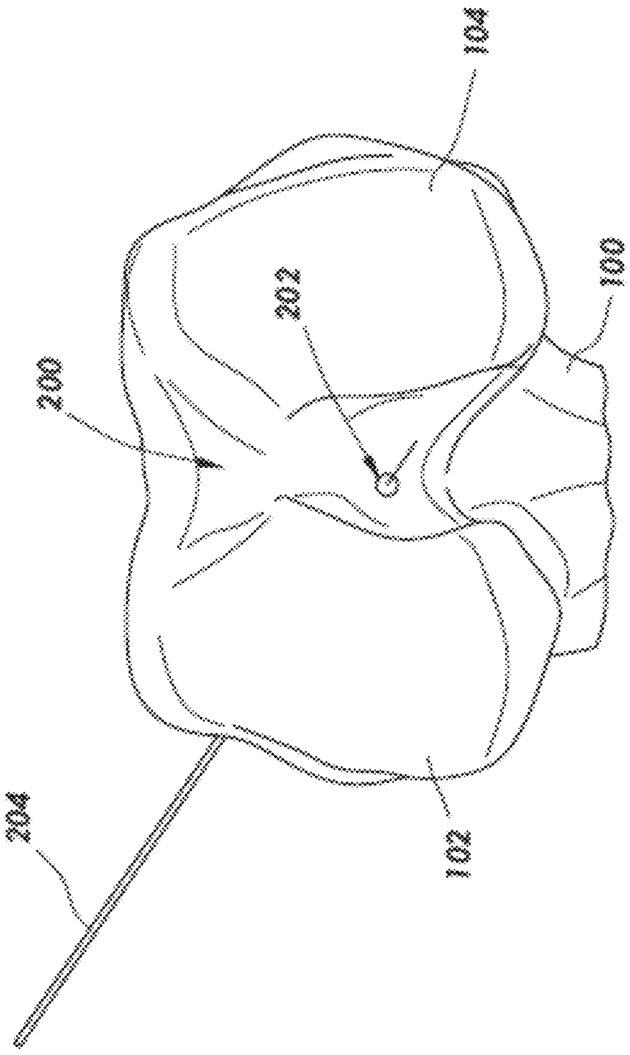
FIG. 3 shows a view of the femur from below and looking into the intercondylar notch.

FIG. 3 shows a view of the femur from below and looking into the intercondylar notch. In particular, visible in FIG. 3 are the lateral condyle 102 and the medial condyle 104. Defined between the femoral condyles 102 and 104 is the femoral notch 200. The femoral tunnel may define an inside aperture 202 within the femoral notch 200, the inside aperture 202 located on wall of the lateral condyle 102 and displaced into the posterior portion of the femoral notch 200. The femoral tunnel extends through the femur 100 and forms an outside aperture on the outside or lateral surface of the femur 100 (the outside aperture not visible in FIG. 3). FIG. 3 shows an example drill wire 204 that may be used to create an initial tunnel or pilot hole. Once the surgeon verifies that the pilot hole is closely aligned with a planned-tunnel path, the femoral tunnel is created by boring or reaming with another instrument (e.g., a reamer) that may use the drill wire 204 as a guide. In some cases, a socket or counter-bore is created on the intercondylar notch side to accommodate the width of the graft that extends into the bone, and that counterbore may also be created using another instrument (e.g., reamer) that may use the drill wire 204 as a guide.

Drilling of a tunnel may take place from either direction. Considering the femoral tunnel again as an example, the tunnel may be drilled from the outside or lateral portion of the femur 100 toward and into the femoral notch 200, which is referred to as an "outside-in" procedure. Oppositely, the example femoral tunnel may be drilled from the inside of the femoral notch 200 toward and to the lateral portion of the femur 100, which is referred as an "inside-out" procedure.

The various examples discussed below are equally applicable to outside-in or inside-out procedures. Outside-in procedures may additionally use a device which holds the drill wire on the outside portion, and physically shows the expected tunnel location of the inside aperture within the knee. However, the device for the outside-in procedure is difficult to use in arthroscopic procedures, and thus many arthroscopic repairs use the inside-out procedure. The further examples discussed below are thus based on an inside-out procedure, but such should not be read as a limitation. The specification now turns to an example surgical system.

Figure 4:
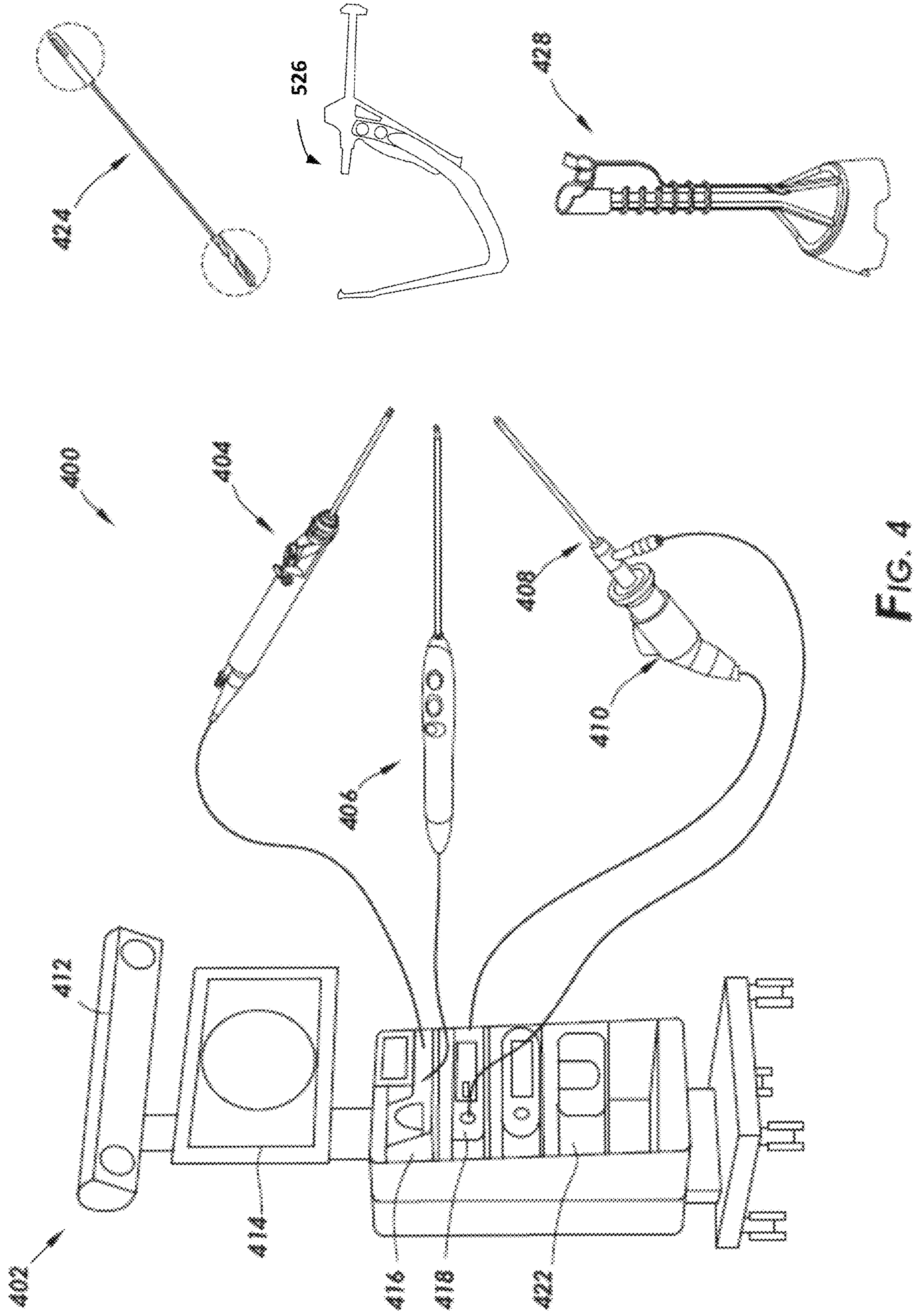
FIG. 4 shows a surgical system in accordance with at least some embodiments.

FIG. 4 shows a surgical system (not to scale) in accordance with at least some embodiments. In particular, the example surgical system 400 comprises a tower or device cart 402, an example mechanical resection instrument 404, an example plasma-based ablation instrument (hereafter just ablation instrument 406), and an endoscope in the example form of an arthroscope 408 and attached camera head 410. The endoscope 408 defines a light connection or light post 420 to which light is provided, and the light is routed internally within the endoscope 408 to illuminate a surgical field at the distal end of the endoscope 408. The device cart 402 may comprise a camera 412 (illustratively shown as a stereoscopic camera), a display device 414, a resection controller 416, and a camera control unit (CCU) together with an endoscopic light source and video controller 418. In example cases the CCU and video controller 418 provides light to the light post 420 of the arthroscope 408, displays images received from the camera head 410. In example cases, the CCU and video controller 418 also implements various additional aspects, such as calibration of the arthroscope and camera head, displaying planned-tunnel paths on the display device 414, receiving revised-tunnel entry locations, calculating revised-tunnel paths, and calculating and displaying various parameters that show the relationship between the revised-tunnel path and the planned-tunnel path. Thus, the CCU and video controller is hereafter referred to as surgical controller 418. In other cases, however, the CCU and video controller may be a separate and distinct system from the controller that handles aspects of intraoperative changes, yet the separate devices would nevertheless be operationally coupled.

The example device cart 402 further includes a pump controller 422 (e.g., single or dual peristaltic pump). Fluidic connections of the mechanical resection instrument 404 and ablation instrument 406 are not shown so as not to unduly complicate the figure. Similarly, fluidic connections between the pump controller 422 and the patient are not shown so as not to unduly complicate the figure. In the example system, both the mechanical resection instrument 404 and the ablation instrument 406 are coupled to the resection controller 416 being a dual-function controller. In other cases, however, there may be a mechanical resection controller separate and distinct from an ablation controller. The example devices and controllers associated with the device cart 402 are merely examples, and other examples include vacuum pumps, patient-positioning systems, robotic arms holding various instruments, ultrasonic cutting devices and related controllers, patient-positioning controllers, and robotic surgical systems.

FIG. 4 further shows additional instruments that may be present during an example ACL repair. In particular, FIG. 4 shows an example guide wire or drill wire 424 and an aimer 526, in this example a tibial aimer. The drill wire 424 may be used to create an initial or pilot tunnel through the bone. In some cases, the diameter of the drill wire may be about 2.4 millimeters (mm), but larger and smaller diameters for the drill wire 424 may be used. The example drill wire 424 is shown with magnified portions on each end, one to show the cutting elements on the distal end of the drill wire 242, and another magnified portion to show a connector for coupling to chuck of a drill. Once the surgeon drills the pilot tunnel, the surgeon and/or the surgical controller 418 (discussed more below) may then assess whether the pilot tunnel matches or closes matches the planned-tunnel path. If the pilot tunnel is deemed sufficient, then the drill wire 424 may be used as a guide for creating the full-diameter throughbore for the tunnel, and possibly also for creating a counterbore associated with intercondylar notch to accommodate the graft. While in some cases the drill wire alone may be used when creating the pilot tunnel, in yet still other cases the surgeon may use the aimer 526 to help guide and place the drill wire 424 at the designed tunnel-entry location.

FIG. 4 also shows that the example system may comprise a calibration assembly 428. As explained in further detail in PCT Publication No. WO/2023/034194 to Quist et al. ("Quist"), the calibration assembly 428 may be used to detect optical distortion in images received by the surgical controller 418 through the arthroscope 408 and attached camera head 410. Additional tools and instruments will be present, such as a drill for drilling with the drill wire 424, various reamers for creating the throughbore and counterbore aspects of the tunnel, and various tools for suturing and anchoring the graft in place. These additional tools and instruments are not shown so as not to further complicate the figure.

The specification now turns to a workflow for an example ACL repair. The workflow may be conceptually divided into a preoperative planning and intraoperative repair. The intraoperative repair workflow may be further conceptually divided into optical system calibration, model registration, intraoperative tunnel-path planning, working portal creation, intraoperative tunnel creation, and intraoperative tunnel placement analysis. Each will be addressed in turn.

Planning

In accordance with various examples, an ACL repair starts with imaging (e.g., X-ray imaging, computed tomography (CT), magnetic resonance imaging (MRI)) of the knee of the patient, including the relevant anatomy like the lower portion of the femur, the upper portion of the tibia, and the articular cartilage. The discussion that follows assumes MRI imaging, but again many different types of imaging may be used. The MRI imaging can be segmented from the image slices such that a volumetric model or three-dimensional model of the anatomy is created. Any suitable currently available, or after developed, segmentation technology may be used to create the three-dimensional model. More specifically to the example of ACL repair and specifically selecting a tunnel path through the femur, a three-dimensional bone model of the lower portion of the femur, including the femoral condyles, is created.

Using the three-dimensional bone model, an operative plan is created that comprises choosing a planned-tunnel path through the femur, including locations of the apertures of the bone that define the ends of the tunnel. For an example inside-out repair, the aperture within the femoral notch is the entry location for the drilling, and the aperture on the lateral surface of the femur is the exit location. For an outside-in repair, the entry and exit locations for drilling are swapped. Still assuming an inside-out repair, the entry location may be selected to be the same as, or close to, the attachment location of the native ACL to the femur within the femoral notch. In some cases, selecting the entry location within the femoral notch may involve use of a Bernard & Hertel Quadrant or grid placed on a fluoroscopic image, or placing the Bernard & Hertel Quadrant on a simulated fluoroscopic image created from the three-dimensional bone model. Based on use of the Bernard & Hertel Quadrant, an entry location for the tunnel is selected. For an inside-out repair, selection of the exit location is less restrictive, not only because the portion of the tunnel proximate to the exit location is used for placement of the anchor for the graft, but also because the exit location is in approximately centered in the femur (considered anteriorly to posteriorly), and thus issues of bone wall thickness at the exit location are of less concern. In some cases, a three-dimensional bone model of the proximal end of the tibia is also created, and the surgeon may likewise choose planned-tunnel path(s) through the tibia.

The results of the planning may comprise: a three-dimensional bone model of the distal end of the femur; a three-dimensional bone model for a proximal end of the tibia; an entry location and exit location through the femur and thus a planned-tunnel path for the femur; and an entry location and exit location through the tibia and thus a planned-tunnel path through the tibia. Other surgical parameters may also be selected during the planning, such as tunnel throughbore diameters, tunnel counterbore diameters and depth, desired post-repair flexion, and the like, but those additional surgical parameters are omitted so as not to unduly complication the specification.

Intraoperative Repair

The specification now turns to intraoperative aspects. The intraoperative aspects include steps and procedures for setting up the surgical system to perform the various repairs. It is noted, however, that some of the intraoperative aspects (e.g., optical system calibration), may take place before any working portals (known also as ports or incisions) are made through the patient's skin, and in fact before the patient is wheeled into the surgical room. Nevertheless, such steps and procedures may be considered intraoperative as they take place in the surgical setting and with the surgical equipment and instruments used to perform the actual repair.

The example ACL repair is conducted arthroscopically and is computer-assisted in the sense the surgical controller 418 is used for arthroscopic navigation within the surgical site. More particularly, in example systems the surgical controller 418 provides computer-assistance during the ligament repair by tracking location of various objects within the surgical site, such as the location of the bone within the internal three-dimensional coordinate space of the view of the arthroscope, and location of the various instruments (e.g., the drill wire 424, the aimer 526) within the internal three-dimensional coordinate space, or "frame", of the view of the arthroscope. Furthermore, in example systems the surgical controller 418 provides computer-assistance during the ligament repair by tracking location of the bone within the external three-dimensional coordinate space of the view of the camera 412 and location of the various instruments and key geometric entities of the instruments such as a points for an instrument tip, a line for axis through an aimer bullet, or a plane, and within the external three-dimensional coordinate space of the view of the camera 412. The specification turns to brief description of such tracking techniques.

Figure 5:
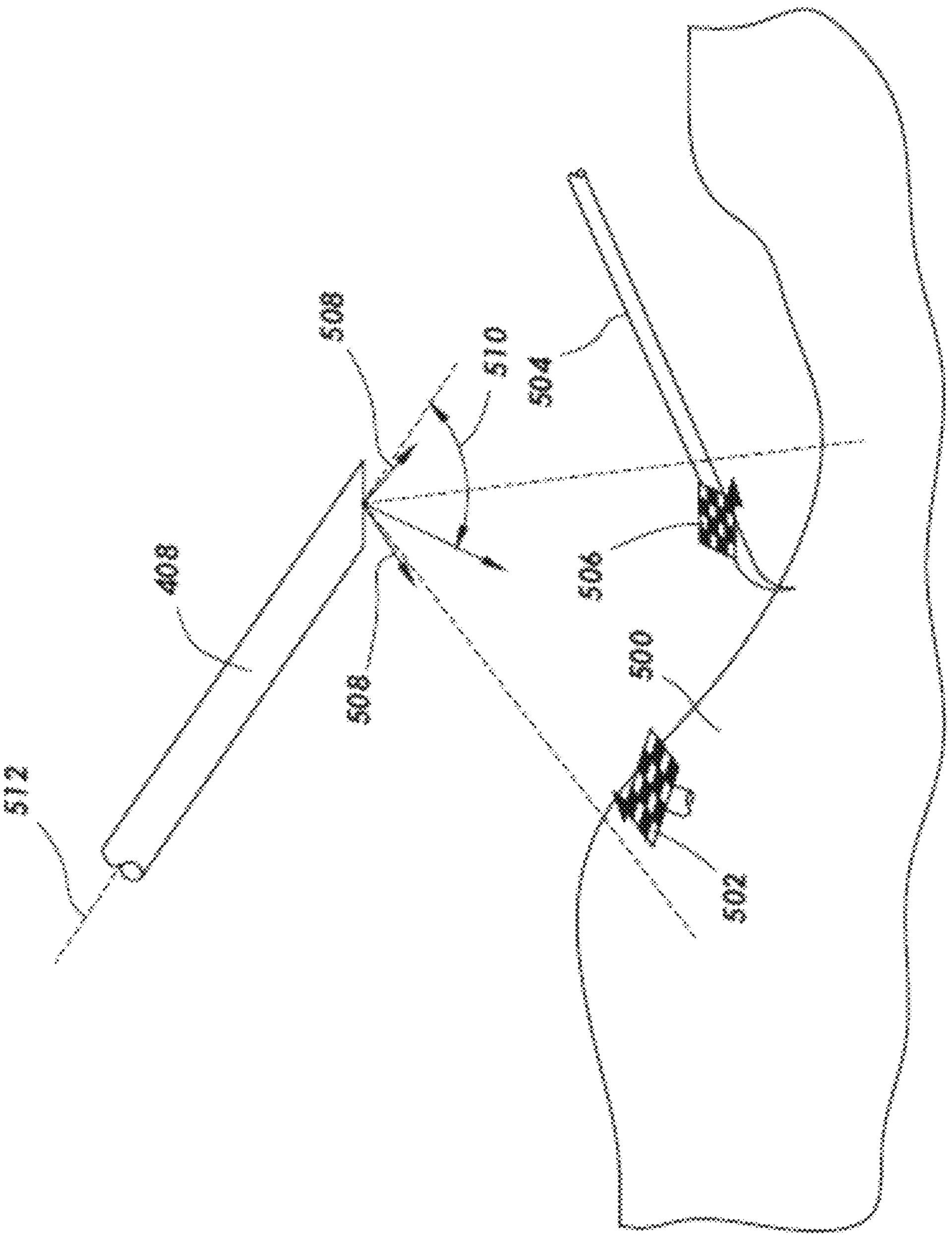
FIG. 5 shows a conceptual drawing of a surgical site with various objects within the surgical site being tracked, in accordance with at least some embodiments.

FIG. 5 shows a conceptual drawing of a surgical site with various objects within the surgical site. In particular, visible in FIG. 5 is a distal end of the arthroscope 408, a portion of a bone 500 (e.g., femur), a bone fiducial 502 within the surgical site, a touch probe 504, and a probe fiducial 506. Each is addressed in turn.

The distal end of the arthroscope 408 is designed and constructed to illuminate the surgical site with visible light received by way of the light post 420 (FIG. 4). In the example of FIG. 5, the illumination is illustrated by arrows 508. The illumination provided to the surgical site is reflected by various objects and tissues within the surgical site, and the reflected light that returns to the distal end enters the arthroscope 408, propagates along an optical channel within the arthroscope 408, and is eventually incident upon a capture array within the camera head 410 (FIG. 4). The images detected by the capture array within the camera head 410 are sent electronically to the surgical controller 418 (FIG. 4) and displayed on the display device 414 (FIG. 4). In accordance with example systems, the arthroscope 408 has a single optical path through the arthroscope for capturing images of the surgical site, notwithstanding that the single optical path may be constructed of two or more optical members (e.g., glass rods, optical fibers). That is to say, in example systems and methods the computer-assisted navigation provided by the arthroscope 408, camera head 410, and surgical controller 418 is provided with the arthroscope 408 that is not a stereoscopic endoscope having two distinct optical paths separated by an interocular distance at the distal end of the endoscope.

During a surgical procedure, a surgeon selects an arthroscope with a viewing direction beneficial for the planned surgical procedure. Viewing direction refers to a line residing at the center of an angle subtended by the outside edges or peripheral edges of the view of an endoscope. The viewing direction for some arthroscopes is aligned with the longitudinal central axis of the arthroscope, and such arthroscopes are referred to as "zero degree" arthroscopes (e.g., the angle between the viewing direction and the longitudinal central axis of the arthroscope is zero degrees). The viewing direction of other arthroscopes forms a non-zero angle with the longitudinal central axis of the arthroscope. For example, for a 30° arthroscope the viewing direction forms a 30° angle to the longitudinal central axis of the arthroscope, the angle measured as an obtuse angle beyond the distal end of the arthroscope. In many cases for ACL repair, the surgeon selects a 30° arthroscope or a 45° arthroscope based on location the port created through the skin of the patient. In the example of FIG. 5, the view angle 510 of the arthroscope 408 forms a non-zero angle to the longitudinal central axis 512 of the arthroscope 408.

Still referring to FIG. 5, within the view of the arthroscope 408 is a portion of the bone 500, along with the bone fiducial 502, the touch probe 504, and the probe fiducial 506. The bone fiducial 502 is shown as a planar element having a pattern disposed thereon, though other shapes for the bone fiducial 502 may be used (e.g., a square block with a pattern on each face of the block). The bone fiducial 502 may be attached to the bone 500 in any suitable form (e.g., a fastener, such as a screw). The pattern of the bone fiducial is designed to provide information regarding the orientation of the bone fiducial 502 in the internal three-dimensional coordinate space of the view of the arthroscope 408. More particularly, the pattern is selected such that the orientation of the bone fiducial 502, and thus the orientation of the underlying bone 500, may be determined from images captured by the arthroscope 408 and attached camera head 410 (FIG. 4).

The probe fiducial 506 is shown as a planar element attached to the touch probe 504. The touch probe 504 may be used, as discussed more below, to "paint" the surface of the bone 500 as part of the registration of the bone 500 to the three-dimensional bone model, and the touch probe 504 may also be used to indicate revised-tunnel entry locations in the case of intraoperative changes to the tunnel paths. The probe fiducial 506 is shown as a planar element having a pattern disposed thereon, though other shapes for the probe fiducial 506 may be used (e.g., a square block surrounding the touch probe 504 with a pattern on each face of the block). The pattern of the probe fiducial 506 is designed to provide information regarding the orientation of the probe fiducial 506 in the internal three-dimensional coordinate space of the view of the arthroscope 408. More particularly, the pattern is selected such that the orientation of the probe fiducial 506, and thus the location of the tip of the touch probe 504, may be determined from images captured by the arthroscope 408 and attached camera head 410 (FIG. 4).

Other instruments within the view of the arthroscope 408 may also have fiducials, such as the drill wire 424 (FIG. 4), a drill, and aimer 426 (FIG. 4), but the additional instruments are not shown in FIG. 5 in particular so as not unduly complicate the figure.

The images captured by the arthroscope 408 and attached camera head 410 are subject to optical distortion in many forms. For example, the visual field between distal end of the arthroscope 408 and the bone 500 within the surgical site is filled with fluid, such as bodily fluids and saline used to distend the joint. Many arthroscopes have one or more lenses at the distal end that widen the field of view, and creating wider field of view causes a "fish eye" effect in the captured images. Further, the optical elements within the arthroscope (e.g., rod lenses) may have optical aberrations inherent to the manufacturing and/or assembly process. Further still, the camera head 410 may have various optical elements for focusing the images receives onto the capture array, and the various optical elements may have aberrations inherent to the manufacturing and/or assembly process. As explained in further detail in Quist, in example systems and methods, prior to use within each surgical procedure, the endoscopic optical system is calibrated to account for the various optical distortions. In an example calibration procedure, the example surgical controller 418 creates a characterization function that characterizes optical distortion between the calibration target and the capture array within the camera head 410. The characterization function may include a calibration for determining orientation of fiducial markers visible within the surgical site (e.g., bone fiducial 502, probe fiducial 506) by way of the arthroscope 408 and attached camera head 410.

The next example step in the intraoperative procedure is the registration of the bone model(s). That is, during the planning stage, imaging (e.g., MRI) of the knee takes place, including the relevant anatomy like the lower portion of the femur, the upper portion of the tibia, and the articular cartilage. The imaging can be segmented such that a volumetric model or three-dimensional model of the anatomy is created from cross-sectional images captured during the imaging. More specifically to the example of ACL repair, and specifically selecting a tunnel path through the femur, a three-dimensional bone model of the lower portion of the femur is created during the planning.

During the intraoperative repair, the three-dimensional bone models and the cross-sectional images are provided to the surgical controller 418. Again using the example of ACL repair, and specifically computer-assisted navigation for tunnel paths through the femur, the three-dimensional bone model of the lower portion of the femur is provided to the surgical controller 418. Thus, the surgical controller 418 receives the three-dimensional bone model, and assuming the arthroscope 408 is inserted into the knee by way of a port through the patient's skin, the surgical controller 418 also receives video images of the femur. In accordance with example methods, the surgical controller 418 may be provided, and thus may receive, the cross-sectional images captured during the planning.

In order to relate the three-dimensional bone model to the images received by way of the arthroscope 408 and camera head 410, the surgical controller 418 registers the three-dimensional bone model to the images of the femur received by way of the arthroscope 408 and camera head 410.

In accordance with example methods, a fiducial marker or bone fiducial (e.g., bone fiducial 502 of FIG. 5) is attached to the femur. The bone fiducial placement is such that the bone fiducial is within the field of view of the arthroscope 408, but in a location spaced apart from the expected tunnel entry/exit point through the lateral condyle. More particularly, in example cases the bone fiducial is placed within the intercondylar notch superior to or above the expected location of the tunnel through lateral condyle.

Figure 6:
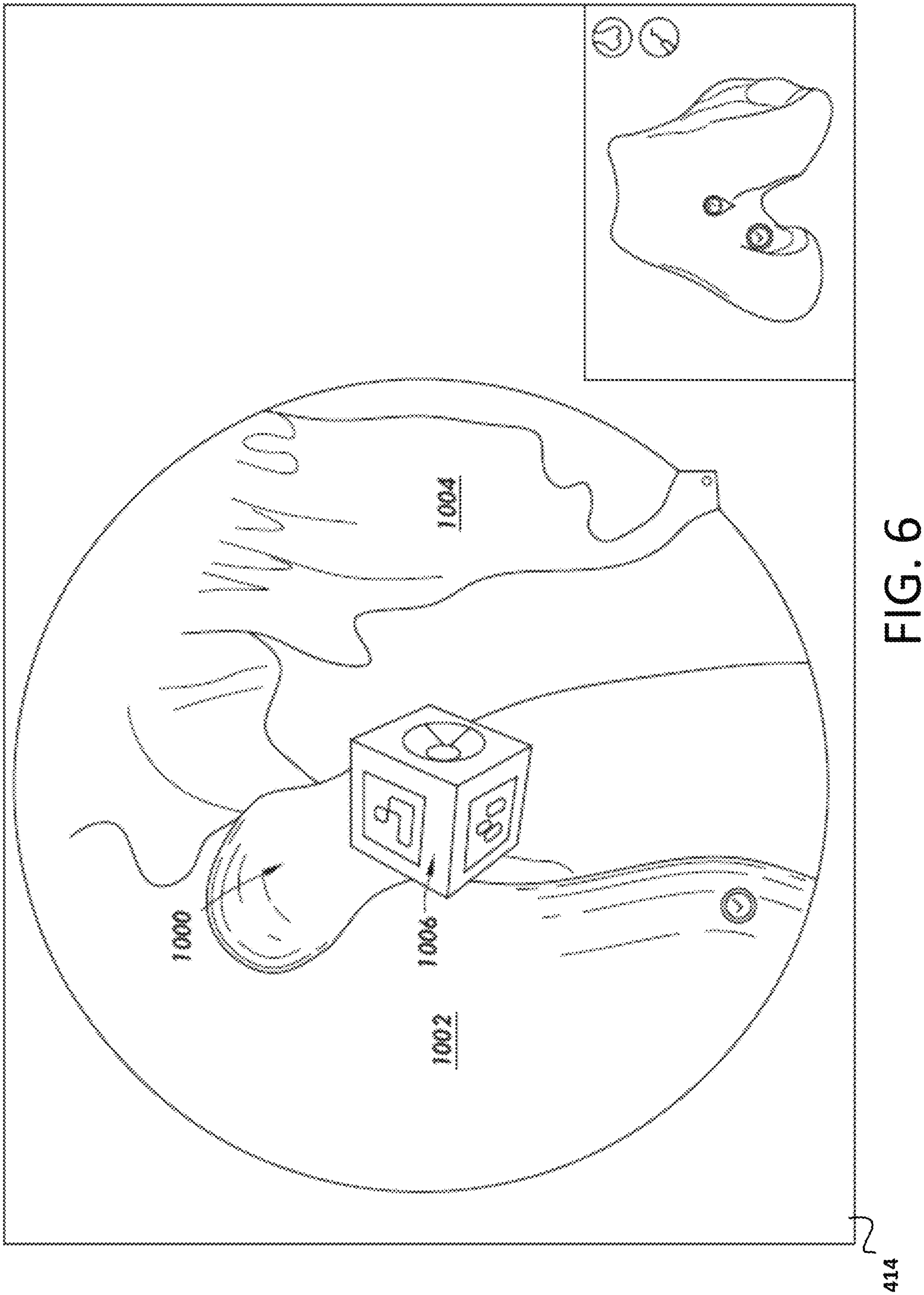
FIG. 6 is an example video display showing portions of a bone and having visible therein a bone fiducial, in accordance with at least some embodiments.

FIG. 6 is an example video display showing portions of a femur and a bone fiducial. The display may be shown, for example, on the display device 414 (FIG. 4) associated with the device cart 402 (FIG. 4), or any other suitable location. In particular, visible in FIG. 6 is a femoral notch or intercondylar notch 1000, a portion of the lateral condyle 1002, a portion the medial condyle 1004, and an example bone fiducial 1006. The bone fiducial 1006 is a fiducial comprising a cube member. Of the six outer faces of the cube member, the bottom face is associated with an attachment feature (e.g., a screw). The bottom face will be close to or will abut the bone when the bone fiducial 1006 is secured in place, and thus will not be visible in the view of the arthroscope 408 (FIG. 4). The outer face opposite the bottom face includes a placement feature used to hold the bone fiducial 1006 prior to placement, and to attach the bone fiducial 1006 to the underlying bone. Of the remaining four outer faces of the cube member (only two of the remaining faces are visible), each of the four outer faces has a machine-readable pattern thereon, and in some cases each machine-readable pattern is unique. Once placed, the bone fiducial 1006 represents a fixed location on the outer surface of the bone in the view of the arthroscope 408, even as the position of the arthroscope 408 is moved and changed relative to the bone fiducial 1006. Initially, the location of the bone fiducial 1006 with respect to the three-dimensional bone model is not known to the surgical controller 418, hence the need for the registration of the three-dimensional bone model.

In order to relate or register the bone visible in the video images to the three-dimensional bone model, the surgical controller 418 (FIG. 4) is provided and thus receives a plurality of locations of an outer surface of the bone. For example, the surgeon may touch a plurality of locations using the touch probe 504 (FIG. 5). As previously discussed, the touch probe 504 comprises a probe fiducial 506 (FIG. 5) visible in the video images captured by the arthroscope 408 (FIG. 4) and camera head 410 (FIG. 4). The physical relationship between the distal end of the touch probe 504 and the probe fiducial 506 is known by the surgical controller 418, and thus as the surgeon touches each of the plurality of locations on the outer surface of the bone, the surgical controller 418 gains an additional "known" location of the outer surface of the bone relative to the bone fiducial 1006. Given that the touch probe 504 is a relatively inflexible instrument, in other examples the tracking of the touch probe 504 may be by optical tracking of an optically-reflective array outside the surgical site (e.g., tracking by the camera 412 (FIG. 4)) yet attached to the portion of the touch probe 504 inside the surgical site.

In some cases, particularly when portions of the outer surface of the bone are exposed to view, receiving the plurality of locations of the outer surface of the bone may involve the surgeon "painting" the outer surface of the bone. "Painting" is a term of art that does not involve application of color or pigment, but instead implies motion of the touch probe 504 when the distal end of the touch probe 504 is touching bone.

Further details of registering a three-dimensional bone model to images of a bone received by way of the arthroscope 408 and camera head 410 will not be described further herein. However, a number of systems, methods and procedures for conducting such registration are described PCT Publication No. WO/2018/170181 to Barreto and Raposo. ("Barreto 2"), and certain aspects are described in other terms in Quist.

Using the three-dimensional bone model, an operative plan may be created that comprises a planned-tunnel path through the bone, including locations of the apertures into the bone that define the ends of the tunnel. In some cases, however, the surgeon may elect not to use planned-tunnel path, and thus elect not to use the planned entry location, exit location, or both. Such an election can be based on any of a number of reasons. For example, intraoperatively the surgeon may not be able to access the entry location for the planned-tunnel path, and thus may need to move the entry location to ensure sufficient access. As another example, during the intraoperative procedure the surgeon may determine that the planned tunnel entry location is misaligned with the attachment location of the native ACL to the femur. Further still, during the intraoperative procedure the surgeon may determine the tunnel entry location is too close to the posterior wall of the femur, increasing the likelihood of a bone chip sometimes referred to as a "back wall blowout." Regardless of the reason for the election to change the tunnel path, in example systems the surgical controller 418 may enable the surgeon to intraoperatively select a revised-tunnel entry, a revised-tunnel exit (if needed), and thus a revised-tunnel path through the bone. A number of systems, methods and procedures for intraoperatively selecting a revised-tunnel entry, a revised-tunnel exit, and thus a revised-tunnel path through the bone are described in Quist.

As discussed herein, it may be useful to track a surgical instrument during a surgical procedure, so that geometric entities of the surgical instrument—such as points and lines corresponding to the surgical instrument the poses of which are useful to track—can be represented on display 414 in the context of the surgical site. In order to track a surgical instrument to be used during a surgical procedure, an instrument fiducial may be physically associated with the surgical instrument. The instrument fiducial may be physically positioned at a location on the surgical instrument that will enter into the surgical site to be seen within the field of view of the arthroscope 408 and attached camera head 410. Alternatively or in some combination, the instrument fiducial may be physically positioned at a location on the surgical instrument that may be visible or otherwise trackable by an external camera system, such as camera 412. The following description focuses on examples in which an instrument fiducial is positioned at a location on the surgical instrument that will enter into the surgical site to be seen with the field of view of the arthroscope 408 and attached camera head 410, though it is not intended that this description be limited to these examples.

As discussed herein, due to the high error tolerances for marking a physical fiducial to be associated with a surgical instrument, or for directly marking the surgical instrument with fiducial markings, the fiducial markings should be calibrated to the surgical instrument. Calibration can be time-consuming, and it can be costly to conduct such calibration at the time of a surgical procedure. Calibration can be conducted prior to the surgical procedure as part of an overall manufacturing-assembly-calibration process. The calibrated surgical instrument can be delivered to a surgeon and simply used by the surgeon without the need to embark on a calibration. Where it may be desirable to re-use a surgical instrument for multiple different surgical procedures, however, processes used for sterilizing the surgical instrument between uses can degrade the fiducial markings themselves and can accordingly reduce overall track-ability of the surgical instrument.

In some examples, each particular instrument fiducial—each unique fiducial—may be calibrated to a digital model of the surgical instrument, in lieu of being calibrated to the actual field instrument with which it is to be physically associated for the surgical procedure. As discussed herein, due to low manufacturing error tolerances typical of CNC machinery and similar machinery, a given surgical instrument manufactured according to the digital model can be, for practical purposes, identical to (in the sense of being interchangeable with) another given surgical instrument manufactured using the same machinery according to the same digital model. For example, the correlation between one surgical instrument and the digital model used to produce it can be practically indistinguishable from the correlation between another surgical instrument and the same digital model. Therefore, if the correlation is known, then an instrument fiducial can be calibrated to the digital model and can serve (with the correlation) as a calibration to any surgical instrument produced using the same machine, and possibly even as a calibration to any surgical instrument produced using the same class or type of machines. It will be appreciated that there may or may not be slight differences between a surgical instrument produced according to the digital model by a first manufacturing machine and a surgical instrument produced according to the digital model by a second manufacturing machine. Being aware during manufacturing and calibration of the correlations between a given surgical instrument produced by each machine and the digital model may be useful for subsequently calibrating instrument fiducials. For example, if more than one manufacturing machine is being used to produce a particular type of, or component of, a surgical instrument a calibration based on the correlation for each of the multiple manufacturing machines may be produced and used by the surgical controller when the unique fiducial is physically associated with the field instrument for use. In this way, any practical variations in production by the multiple manufacturing machines may be taken into account.

There is likely to be no practical difference between a first surgical instrument produced by a given manufacturing machine and a second surgical instrument produced by the same given manufacturing machine. Furthermore, while a manufacturer would wish to confirm and ensure there was no production drift, there may indeed be no practical difference between a first surgical instrument produced by a given manufacturing machine and a second surgical instrument produced by a different manufacturing machine that is of the same type/setup/class as the other.

Therefore, according to this description, calibration to the digital model of the surgical instrument can serve as a calibration to the field instrument itself. By enabling each unique fiducial to be calibrated in the absence of the field instrument with which it will be physically associated, manufacture, delivery, handling and sterilizing of the field instrument may be conducted relatively independently of the unique fiducial(s) that are to be used with the field instrument. For example, a surgeon may be the one to physically associate a unique fiducial with the field instrument and to ensure the surgical controller has, or can retrieve, the calibration data for that unique fiducial. The surgeon may then proceed to conduct the surgical procedure using the field instrument. After the surgical procedure, the surgeon may dissociate that unique fiducial from the field instrument and subject the field instrument to sterilization. At the time of a subsequent surgical procedure that will make use of that same field instrument, the surgeon may physically associate another unique fiducial with the field instrument and ensure the surgical controller has, or can retrieve, the calibration data for that other unique fiducial.

It will be appreciated that each unique fiducial may be intended to have the same visual markings as another unique fiducial. For example, a set of unique fiducials may have markings that enable a surgical controller to be aware after image processing that these fiducials represent a particular tibial aimer, and differently-marked fiducials represent a particular drill tip, and so forth. However, in this description due to high manufacturing tolerances even a set of fiducials that are intended to be identical may tend in reality, due to high manufacturing tolerances for marking, to be slightly different, and thus unique in the sense that a given marking on one unique fiducial may vary slightly and in a consequential way in dimension or positioning/orientation on the substrate on which it is marked from what is intended to be the same given marking on another of the fiducials.

Figure 7A:
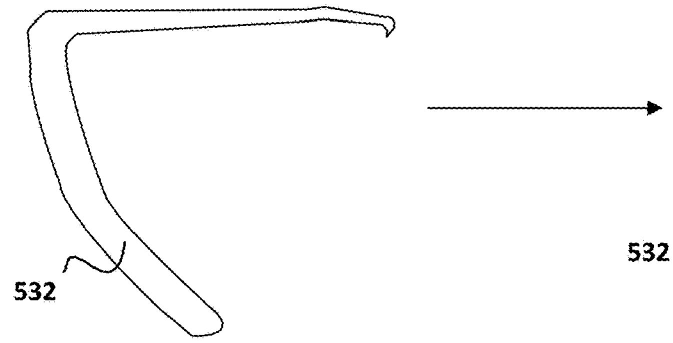
FIGS. 7A-7D show a component of a calibration instrument to which an unique fiducial that will be physically associated with a field instrument is attached for calibration, the registration of the calibration instrument carrying the unique fiducial to a digital model of the field instrument, and a representation of a pose for each geometric entity of the digital model with respect to the unique fiducial after calibration.

FIG. 7A shows a calibration component to be used for the calibration of an unique fiducial. In this example, the field instrument is a tibial aimer, and the calibration component is a calibration aimer arm 532 that has been physically manufactured in accordance with a digital model of the tibial aimer, or at least in accordance with a digital model of the aimer arm of the tibial aimer. It will be appreciated that in this description a digital model of a field instrument may take the form of multiple digital models each of a respective component of the field instrument. In the case of a tibial aimer, an aimer arm and a handle may each be separately manufactured and then assembled together to complete the tibial aimer in which the aimer arm can assume different states with respect to the handle. Therefore, a digital model of an aimer arm for a tibial aimer may be stored in memory separately from a digital model of a handle for the tibial aimer, so that a different manufacturing machine may be used to manufacture each, or so that a single manufacturing machine may be used to manufacture each at different times. A single digital model of a tibial aimer may alternatively incorporate sub-models of the aimer arm and the handle for such a purpose.

Figure 7B:
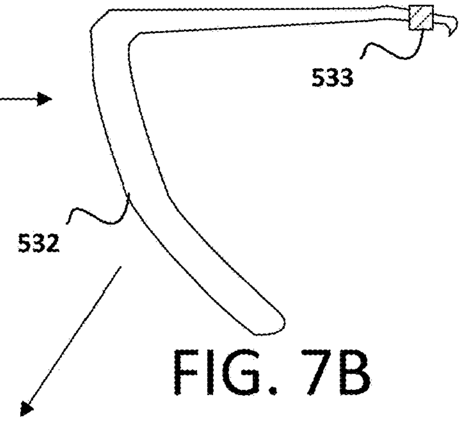

FIG. 7B shows an unique fiducial 533 having been physically associated with calibration aimer arm 532. Unique fiducial 533 is shown in this and in other figures as a square, simply for ease of illustration, and is not shown to scale with respect to calibration aimer arm 532. Unique fiducial 533 may, for example, be a smaller, cube- or other 3D-shaped fiducial with fiducial markings on each of several faces.

In this example, unique fiducial 533 includes an attachment feature (not shown) enabling unique fiducial 533 to be physically associated with, and dissociated from, calibration aimer arm 532 and with/from a field instrument. Such an attachment feature may be a threaded male component extending from unique fiducial 533 that may be threaded into, and later out of, a corresponding threaded female attachment feature (not shown) at a fixed position on calibration aimer arm 532/field instrument.

It will be appreciated that the location at which unique fiducial 533 is physically associated with calibration aimer arm 532 is close to features of the calibration aimer arm 532 that correspond to features of a field instrument that will enter into a surgical site and that accordingly can be captured within the field of view of arthroscope 408 and attached camera head 410. In this way, unique fiducial 533, when eventually physically associated with a field instrument, can also be captured within the field of view to enable surgical guidance to incorporate the field instrument and its key geometric entities.

Unique fiducial 533 is temporarily physically associated with calibration aimer arm 532 so that unique fiducial 533 may be calibrated to a digital model of a field aimer arm using calibration aimer arm 532.

Figure 7C:
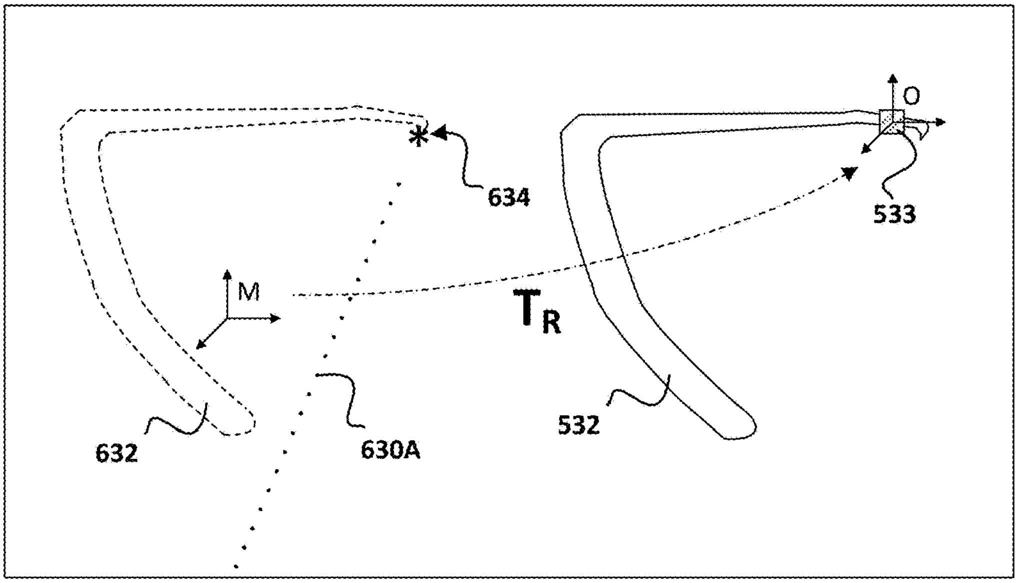

FIG. 7C shows a representation of a digital model 632 of the aimer arm. Digital model 632 has a coordinate system, or frame, "M", in which key geometric entities 634 and 630A are positioned and oriented (or "posed"). In particular, in digital model 632, geometric entities 634 and 630A each have a 3D position and orientation (a "pose") with respect to a 3D origin of coordinate system M. In this example, geometric entity 634 is a point at the tip of the aimer arm that digital model 632 represents, and geometric entity 630A is a line extending through a bullet (not shown) of the tibial aimer with respect to digital model 632.

Figure 7D:
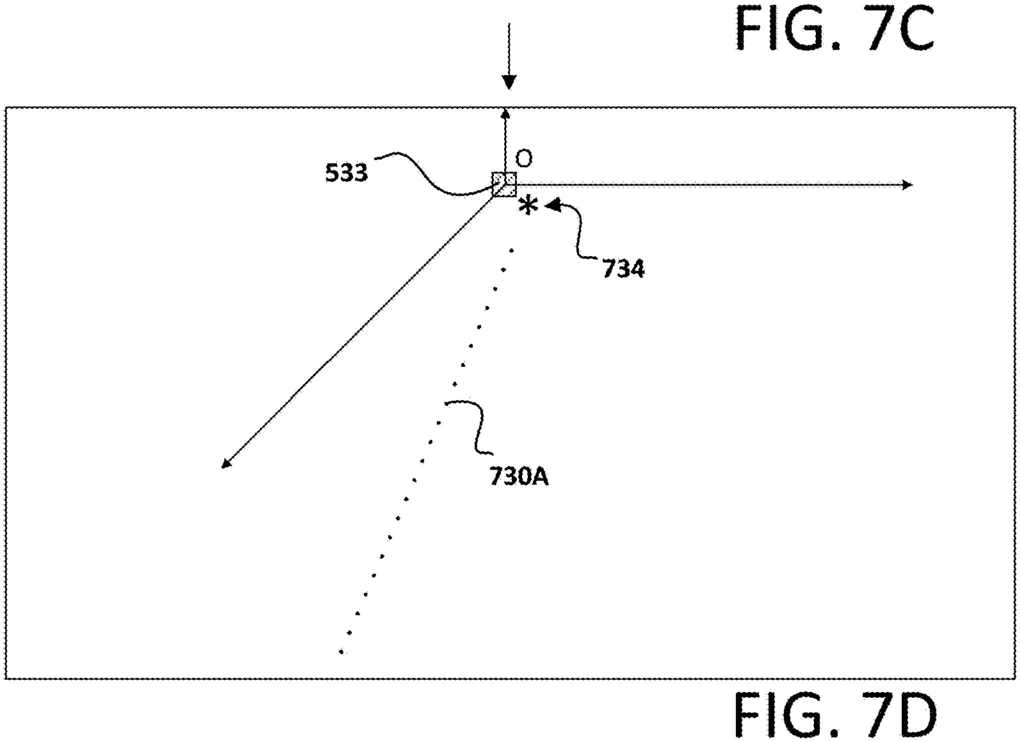

In FIG. 7C, a dashed line labelled "$T_R$" is shown, and represents a transformation between the coordinate system M of the digital model 632 and the coordinate system O of unique fiducial 533. This transformation is determined through a process of selecting multiple points on digital model 632 and identifying, for each of the selected points, their counterpart point on calibration aimer arm 532 as represented within the coordinate system O, thereby to produce respective point pairs. That is, when unique fiducial 533 is physically associated as shown with calibration aimer arm 532, unique fiducial 533 provides a coordinate system O for calibration aimer arm 532. As such, a point along calibration arm 532 in coordinate system O can be identified for each of a plurality of points along digital model 632 in coordinate system M. Such points along calibration arm 532 may be identified using machine vision by capturing video frames of calibration arm 532 and associated unique fiducial 533 while a pointer (having its own fiducial or otherwise uniquely identifiable in video frames) is touched to various corresponding points along calibration arm 532. Such video frames may then be processed. When a sufficient number of point pairs are captured, the pairs may be registered to produce an overall M-to-O transformation $T_R$. With transformation $T_R$ having been produced, a pose for each of the geometric entities 634, 630A in the frame M, may be calculated based on the transformation $T_R$ in the frame O as corresponding poses of geometric entities 734, 730A. FIG. 7D shows poses of geometric entities 734, 730A in frame O of unique fiducial 533 corresponding respectively to the poses of geometric entities 634, 630A in frame M of the digital model.

The poses of the geometric entities 734, 730A in the frame O may thereafter be stored as geometric entity data in computer-readable memory in the form of an unique calibration data file encoding one or more matrices, datapoints, or some other data structure(s) in association with an unique identifier for the unique fiducial 533. The newly-calculated poses may be thought of as being "carried" with unique fiducial 533. In particular, later, after unique fiducial 533 is dissociated from calibration aimer arm 532, eventually reaches a surgical room and is physically associated with a field instrument, the calibration data file may be retrieved by the surgical controller or otherwise made available to the surgical controller using the unique identifier. In this way, surgical controller is equipped to interpret, in video frames, a pose of unique fiducial 533 as imparting its frame 533 to the field instrument itself, such that the poses of geometric entities 734, 730A correspond to the physical positions/orientations of the geometric entities of the field instrument itself. In particular, during surgery, by processing images containing unique fiducial 533, and having retrieved or been otherwise provided with the geometric entity data, the surgical controller can conduct various operations based on an awareness of the poses of the actual geometric entities of the field instrument with respect to the surgical site.

The above-noted procedure may be conducted in the same manner for each of a number of instances of the unique fiducial, so that each instance may itself have one or more respective geometric entities that may be individually retrieved or otherwise made available to a surgical controller. While the present description is directed to addressing the problem of high error tolerances in marking processes, in the event that manufacture of markings for fiducials can reach as low an error tolerance as that for instruments with which they are to be associated, then calibration of an instance of an unique fiducial to a digital model of the instrument fiducial itself can serve as a calibration of all instances of that unique fiducial to the surgical tools with which they may eventually be physically associated.

The above example of generating geometric entity data is useful for unique fiducials that are intended to be physically associated with surgical instruments that have a single state. It will be appreciated that, though the tibial aimer was used as an example, a tibial aimer typically is adjustable by virtue of movement of its aimer arm to different positions with respect to its handle, even while the aimer arm is retained within the handle. Therefore, certain surgical tools, such as tibial aimers, may be configured to assume multiple physical states.

Figure 8A:
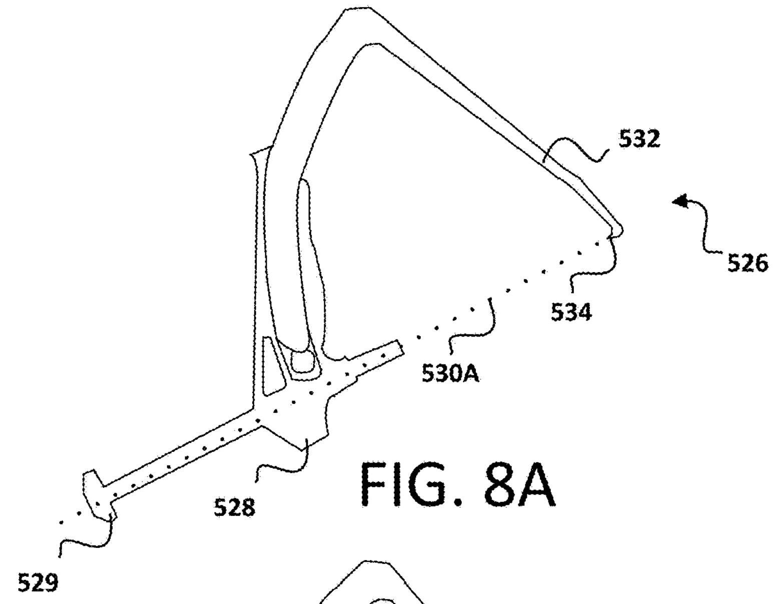
FIGS. 8A-8C show a field instrument in respective different states, corresponding to at least one geometric entity of the field instrument having respective different poses.

FIG. 8A shows a field instrument—a tibial aimer 526—in a first state in which aimer arm 532 is at a first position with respect to handle 528. A point 534 corresponds to the tip of the aimer arm 532, and a line 530A corresponds to the axis through a bullet 529 integral with handle 528 while the aimer arm 532 is in the first position.

Figure 8B:
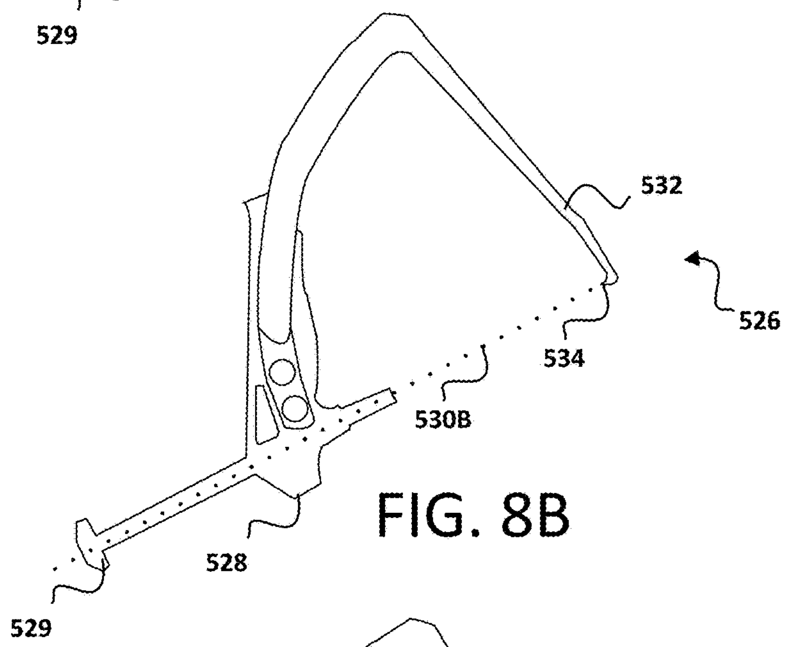
Figure 8C:
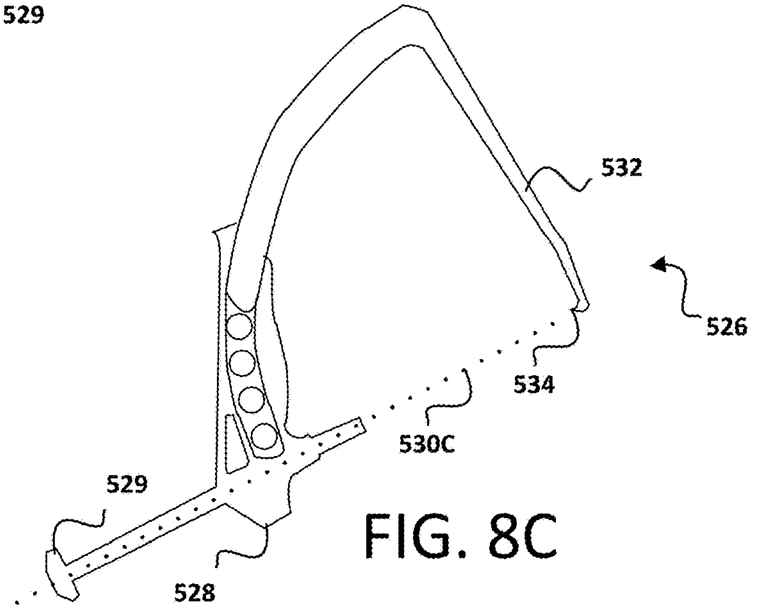

By design, with respect to both aimer arm 532 and handle 528 the point 534 of the tip of aimer arm 532 will not change if aimer arm 532 and handle 528 are positioned differently with respect to each other. However, it will be appreciated that, while—with respect to handle 528—the axis through bullet 529 does not change even when aimer arm 532 is moved to another position with respect to handle 528, it is the case that—with respect to aimer arm 532—the axis through bullet 529 will indeed change when aimer arm 532 is moved to another position. Therefore, if in order to ensure an unique fiducial is within the field of view of an arthroscope 408 and its camera head 410 the unique fiducial is located on aimer arm 532, the axis through bullet 529 will change with respect to the unique fiducial depending on the position of aimer arm 532 with respect to handle 528. FIG. 8B shows the tibial aimer 526 of FIG. 8A, but in this figure in a second state in which aimer arm 532 is at a second position with respect to handle 528. Point 534 still corresponds to the tip of the aimer arm 532, but a line 530B corresponds to the axis through bullet 529 while the aimer arm 532 is in the second position. FIG. 8C shows the tibial aimer 526 of FIGS. 8A and 8B, but in this figure in a third state in which aimer arm 532 is at a third position with respect to handle 528. Point 534 still corresponds to the tip of the aimer arm 532, but a line 530C corresponds to the axis through bullet 529 while the aimer arm 532 is in the third position. It is the case, therefore, that the pose of the axis through bullet 529 with respect to aimer arm 532 and thus with respect to the unique fiducial that is to be physically associated with aimer arm 532, depends on the position of the aimer arm 532 with respect to handle 528. Accordingly, it is the case that multiple different states of a field instrument should be taken into account when calibrating an unique fiducial to the digital model of the field instrument.

The digital model of the field instrument may itself include a number of different poses for a given geometric entity. For example, a digital model of a tibial aimer may include a number of predefined lines corresponding to the bullet axis with respect to the aimer arm for each of a number of different predefined positions of the aimer arm with respect to the handle. When a field tibial aimer takes one of the positions, then geometric entity data corresponding to that position can be used to calculate the pose of the geometric entity in the surgical site.

Poses of a geometric entity in a digital model may take different forms. To take the tibial aimer example, while the digital model may include a fixed set of poses for a bullet axis, each corresponding to respective relative position of the aimer arm and the handle, the digital model may alternatively include a formula that can compute the pose of a line through the bullet axis given a particular position of the aimer arm in a range of positions with respect to the handle. Therefore, instead of predefining fixed positions, the surgeon can have more flexibility in choosing a physical position (i.e. a state) during a surgical procedure, as desired, and the pose of the bullet axis line with respect to the surgical site can be calculated based on the chosen physical position using the formula in the geometric entity data and the pose of the unique fiducial being captured within the field of view of the arthroscope 408 and the attached camera head 410.

Figure 9A:
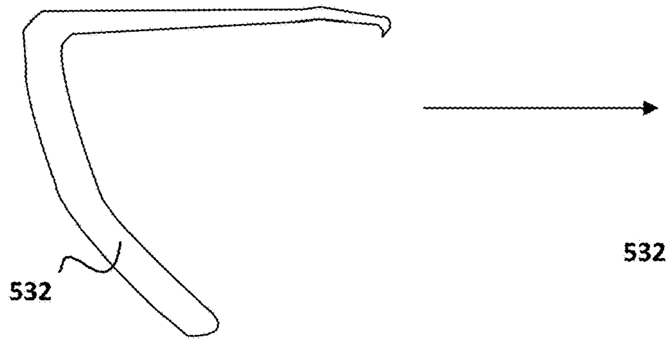
FIGS. 9A-9D show a component of a calibration instrument to which an unique fiducial that will be physically associated with a field instrument is attached for calibration, the registration of the unique fiducial to a digital model of the field instrument, and a representation of poses of geometric entities of the digital model with respect to the unique fiducial after calibration.
Figure 9B:
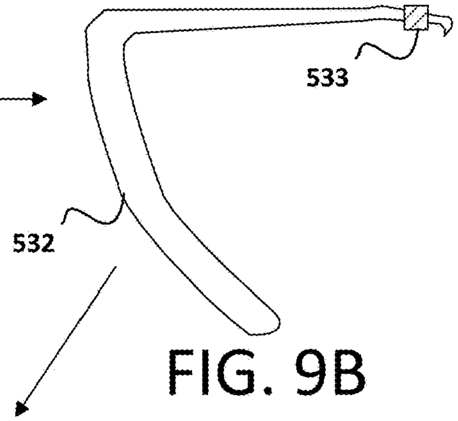

FIG. 9A shows a calibration component to be used for the calibration of an unique fiducial. In this example, the field instrument is a tibial aimer, and the calibration component is a calibration aimer arm 532 that has been physically manufactured in accordance with a digital model of the tibial aimer, or at least in accordance with a digital model of the aimer arm of the tibial aimer. FIG. 9B shows an unique fiducial 533 having been physically associated with calibration aimer arm 532. Unique fiducial 533 is shown in this and in other figures as a square, simply for ease of illustration, and is not shown to scale with respect to calibration aimer arm 532. Unique fiducial 533 may, for example, be a smaller, cube- or other 3D-shaped fiducial with fiducial markings on each of several faces.

In this example, unique fiducial 533 includes an attachment feature (not shown) enabling unique fiducial 533 to be physically associated with, and dissociated from, calibration aimer arm 532 and with/from a field instrument. Such an attachment feature may be a threaded male component extending from unique fiducial 533 that may be threaded into, and later out of, a corresponding threaded female attachment feature (not shown) at a fixed position on calibration aimer arm 532/field instrument.

It will be appreciated that the location at which unique fiducial 533 is physically associated with calibration aimer arm 532 is close to features of the calibration aimer arm 532 that correspond to features of a field instrument that will enter into a surgical site and that accordingly can be captured within the field of view of arthroscope 408 and attached camera head 410. In this way, unique fiducial 533, when eventually physically associated with a field instrument, can also be captured within the field of view to enable surgical guidance to incorporate the field instrument and its key geometric entities.

Unique fiducial 533 is temporarily physically associated with calibration aimer arm 532 so that unique fiducial 533 may be calibrated to a digital model of a field aimer arm using calibration aimer arm 532.

Figure 9C:
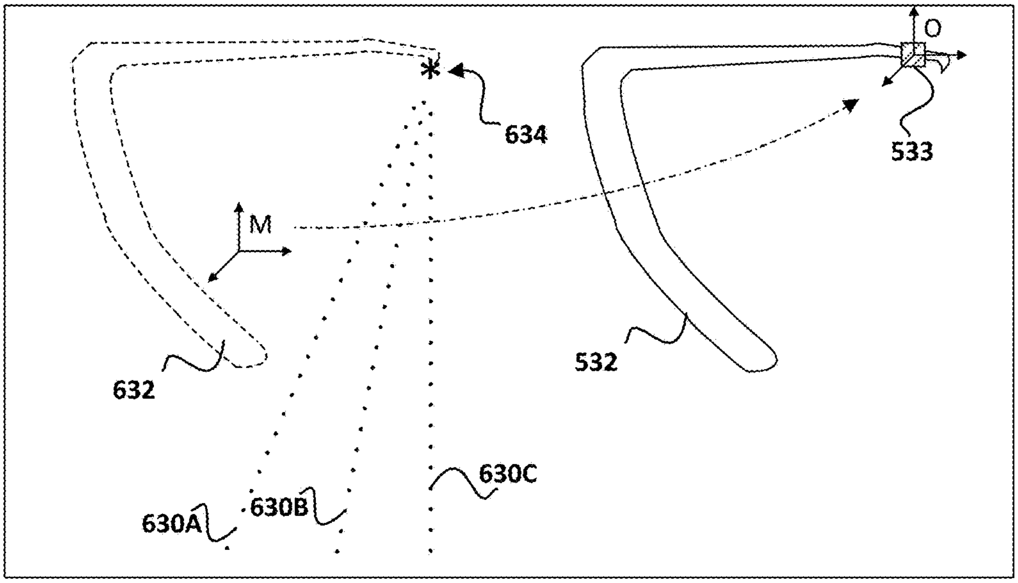
Figure 9D:
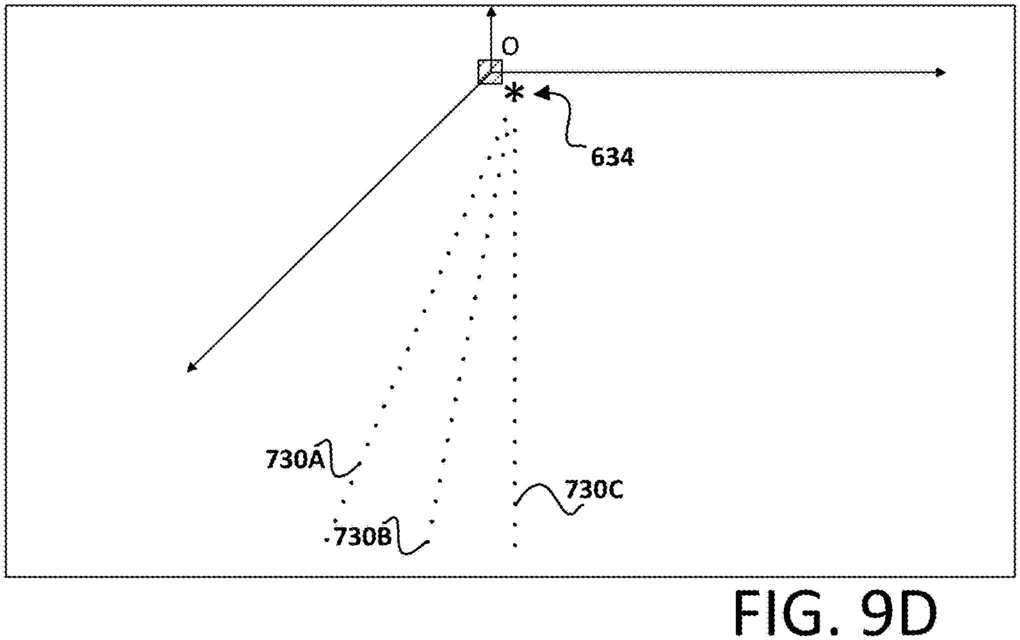

FIG. 9C shows a representation of a digital model 632 of the aimer arm. Digital model 632 has a coordinate system, or frame, "M", in which key geometric entities 634, 630A, 630B, and 630C are positioned and oriented (or "posed"). In particular, in digital model 632, geometric entities 634, 630A, 630B, 630C each have a 3D position and orientation (a "pose") with respect to a 3D origin of coordinate system M. In this example, like in the example given in connection with FIGS. 7A to 7D, geometric entity 634 is a point at the tip of the aimer arm that digital model 632 represents. However, multiple geometric entities correspond to a line extending through the bullet (not shown) of the tibial aimer. In particular, geometric entity 630A is a line extending through the bullet with respect to digital model 632 when its aimer arm is at a first position with respect to its handle. Also, geometric entity 630B is a line extending through the bullet of the tibial aimer with respect to digital model 632 when its aimer arm is at a second position with respect to its handle. Similarly, geometric entity 630B is a line extending through the bullet of the tibial aimer with respect to digital model 632 when its aimer arm is at a third position with respect to its handle.

In FIG. 9C, a dashed line labelled "$T_R$" is shown, and represents a transformation between the coordinate system M of the digital model 632 and the coordinate system O of unique fiducial 533. This transformation is determined through a process of selecting multiple points on digital model 632 and identifying, for each of the selected points, their counterpart point on calibration aimer arm 532 as represented within the coordinate system O, thereby to produce respective point pairs. That is, when unique fiducial 533 is physically associated as shown with calibration aimer arm 532, unique fiducial 533 provides a coordinate system O for calibration aimer arm 532. As such, a point along calibration arm 532 in coordinate system O can be identified for each of a plurality of points along digital model 632 in coordinate system M. Such points along calibration arm 532 may be identified using machine vision by capturing video frames of calibration arm 532 and associated unique fiducial 533 while a pointer (having its own fiducial or otherwise uniquely identifiable in video frames) is touched to various corresponding points along calibration arm 532. Such video frames may then be processed. When a sufficient number of point pairs are captured, the pairs may be registered to produce an overall M-to-O transformation $T_R$. With transformation $T_R$ having been produced, a pose for each of the geometric entities 634, 630A, 630B, 630C in the frame M, may be calculated based on the transformation $T_R$ in the frame O as corresponding poses of geometric entities 734, 730A, 730B, 730C. FIG. 7D shows poses of geometric entities 734, 730A, 730B, 730C in frame O of unique fiducial 533 corresponding respectively to the poses of geometric entities 634, 630A, 630B, 630C in frame M of the digital model.

Transformation $T_R$ and the poses of the geometric entities 734, 730A, 730B, 730C in the frame O may thereafter be stored as geometric entity data in computer-readable memory in the form of an unique calibration data file encoding one or more matrices, datapoints, or some other data structure(s) in association with an unique identifier for the unique fiducial 533. The newly-calculated poses may be thought of as being "carried" with unique fiducial 533. In particular, later, after unique fiducial 533 is dissociated from calibration aimer arm 532, eventually reaches a surgical room and is physically associated with a field instrument, the calibration data file may be retrieved by the surgical controller or otherwise made available to the surgical controller using the unique identifier. In this way, surgical controller is equipped to interpret, in video frames, a pose of unique fiducial 533 as imparting its frame 533 to the field instrument itself, such that the poses of geometric entities 734, 730A, 730B, 730C correspond to the physical positions/orientations of the geometric entities of the field instrument itself. In particular, during surgery, by processing images containing unique fiducial 533, and having retrieved or been otherwise provided with the geometric entity data as well as having been made aware of the actual state of the field instrument (i.e., for a tibial aimer, the position of the aimer arm with respect to the handle), the surgical controller can conduct various operations based on an awareness of the poses of the actual geometric entities of the field instrument with respect to the surgical site.

The above-noted procedure may be conducted in the same manner for each of a number of instances of the unique fiducial, so that each instance may itself have a respective transformation $T_R$ that may be individually retrieved or otherwise made available to a surgical controller.

While a given instance of a unique fiducial can be calibrated to a digital model of a surgical image by collecting point pairs for each unique fiducial as described herein, alternatives are possible. For example, rather than collecting point pairs using points along the calibration instrument for each and every unique fiducial to be calibrated, a single session of collecting point pairs using points along the calibration instrument to determine a transformation for a more permanent fiducial (or "calibration fiducial") affixed to the calibration instrument may be conducted. This single session generates a first intermediate transformation from the frame of the calibration instrument, as imparted by the calibration fiducial, to the frame of the digital model. Then, in turn, each unique fiducial may be also physically associated, along with the calibration fiducial, with the calibration instrument and a second intermediate transformation generated as between the unique fiducial and the calibration fiducial. The unique transformation $T_R$ for each unique fiducial then is a combination of the first intermediate transformation and the unique second intermediate transformation conducted for the unique fiducial. Because the second intermediate transformation can be conducted by capturing just one image of both the calibration fiducial and the unique fiducial to be individually calibrated, it can typically be done in less time for each successive unique fiducial than capturing point pairs for each unique fiducial for the calibration.

Figure 10:
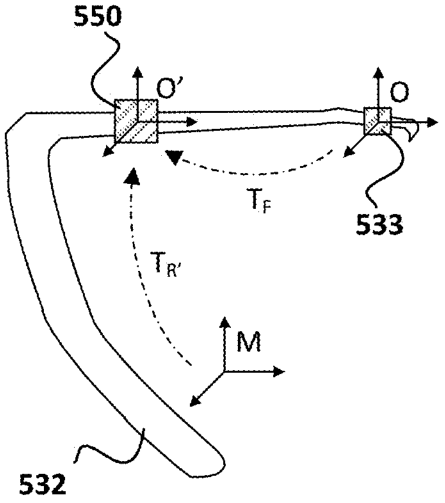
FIG. 10 shows a calibration instrument to which a unique fiducial may be temporarily affixed for calibration, with the calibration being conducted by generating a transformation from the unique fiducial to a calibration fiducial that is affixed to the calibration tool.

FIG. 10 shows a calibration instrument 532 to which a unique fiducial 533 may be temporarily affixed for calibration, with the calibration being conducted by generating a transformation from the unique fiducial 533 to a calibration fiducial 550 that is affixed to the calibration tool 532. A transformation $T_{R'}$ as between the frame M of the digital model and a frame O' of the calibration instrument 532 is generated once using the point pair method described herein, or some other method. For each unique fiducial 533, a transformation $T_F$ is generated by capturing both calibration fiducial 550 and unique fiducial 533 in at least one image and processing the at least one image. With both $T_{R'}$ and $T_F$, the unique transformation $T_R$ for the unique fiducial may be calculated as in Equation 1, below:

$$T_R = T_{R'} T_F \tag{1}$$

Based on a unique transformation $T_R$ for each unique fiducial (i.e., $T_{R1}$, $T_{R2}$, $T_{R3}$ . . . . $T_{Rn}$ for n different unique fiducials), the pose or poses of each geometric entity in the digital model with respect to the frame O of each unique fiducial may be calculated.

Where it is required and/or desirable to directly mark a surgical instrument with fiducial markings, and where the marking is done to a high error tolerance, the directly-marked fiducial markings are required to be calibrated to the surgical instrument on which they are marked. The benefits of re-use through multiple sterilizations and the association of a replacement unique fiducial for each successive procedure as described herein may not be available for a directly-marked surgical instrument. However, the principle described herein, whereby poses of geometric entities may be thought of as "carried" by a fiducial as a result of one or more transformations, may be beneficial for reducing the time for calibrating surgical instruments to the fiducial markings made thereon.

Figures 11A, 11B, 11C, 11D, 11E, 11F:
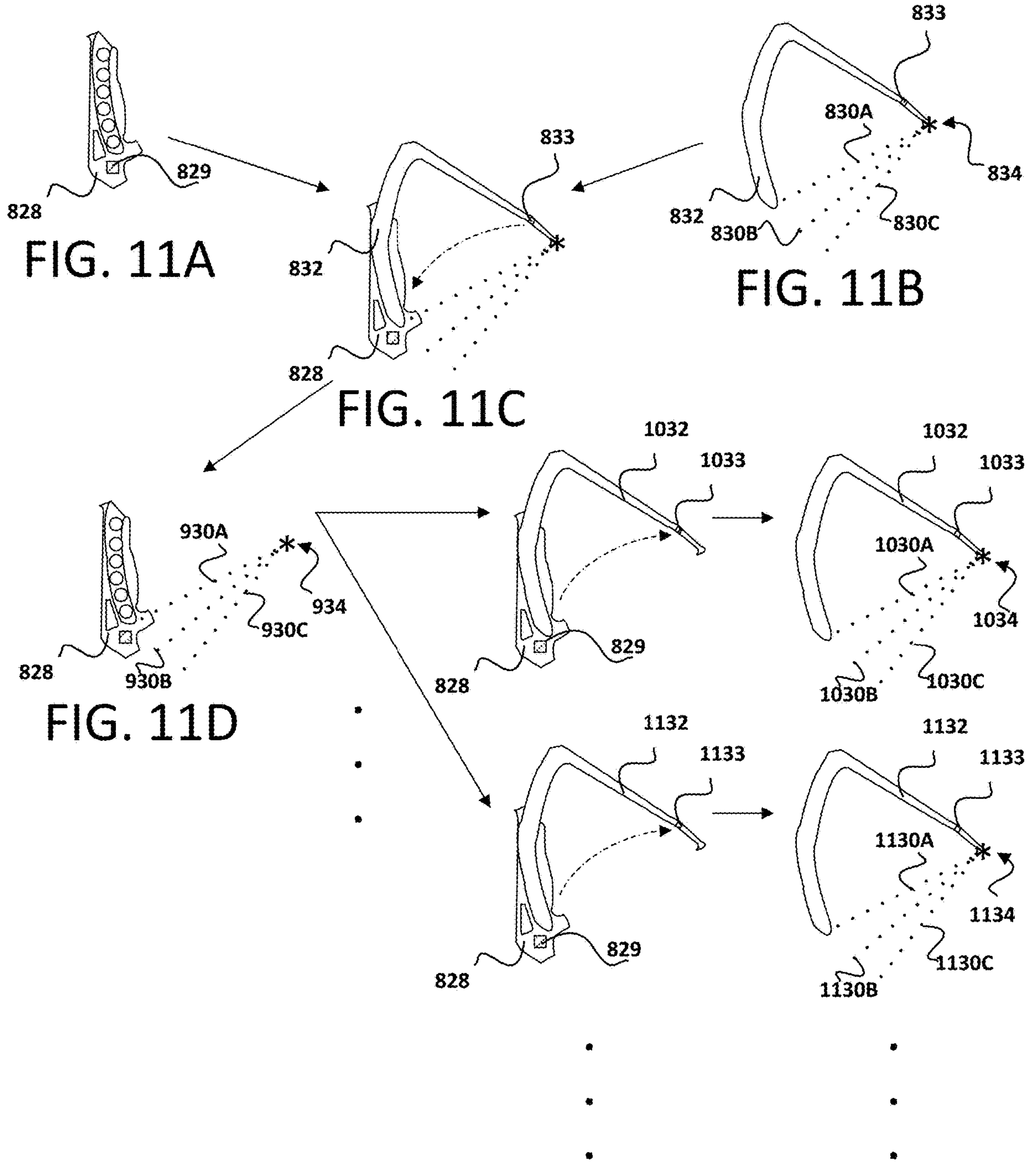
FIGS. 11A-11F show representations of a method in which a component of a field instrument that is affixed with a unique fiducial is calibrated using a calibration jig.

FIGS. 11A-11F show visual representations of a method in which a component of a field instrument that is affixed with a unique fiducial is calibrated using a calibration jig based on the principle of geometric entities being carried by a fiducial. In particular, FIG. 11A shows a calibration handle 828 having a calibration fiducial 829 affixed to or marked thereon. Calibration handle 828 may be manufactured in accordance with a digital model of a surgical instrument, in this example of a tibial aimer. It will be appreciated that calibration handle 828 does not need, for the purpose of calibration of a field instrument or portion thereof, a bullet. FIG. 11B shows a calibration aimer arm 832 having a calibration fiducial 833 marked thereon. Geometric entities 834, 830A, 830B and 830C corresponding respectively to the tip of calibration aimer arm 832 and three poses of the bullet, having known poses in the frame of calibration fiducial 833. This may have been achieved by calibrating calibration fiducial 833 itself to a digital model of the tibial aimer or of its aimer arm in particular. However, it is desirable to transfer these poses to the frame of calibration handle 828 that is imparted to calibration handle by calibration fiducial 829. Once done, calibration handle 828 may be deployed as a calibration jig that can, in turn, transfer these poses to the unique frames of each of a plurality of newly manufactured and marked aimer arms to be used in the field.

In FIG. 11C, calibration aimer arm 832 is physically associated with handle 828 serving as a calibration jig, and seated within handle 828. The arrowed dashed-line represents a first transformation from a frame L of calibration fiducial 833 to a frame M of calibration handle 828, which may be conducted by capturing at least one image of both calibration fiducial 833 and calibration fiducial 829 while calibration aimer arm 832 is seated in handle 828 (or otherwise positioned in a precise predefined position with respect to handle 828), and processing the at least one image. This particular transformation informs a transformation of the poses of geometric entities 834, 830A, 830B, 830C in the frame of calibration fiducial 833 to the frame of calibration fiducial 829 of calibration handle 828. FIG. 11D shows calibration handle 828 with calibration aimer arm 833 having been physically dissociated from it, and poses of the geometric entities transferred from calibration aimer arm 832 to the frame of calibration handle, therein identified as geometric entities 934, 930A, 930B, 930C. The poses of geometric entities 934, 930A, 930B, 930C represented in the frame of calibration fiducial 829 on calibration handle 828 may thereafter be transferred to multiple field user aimer arms.

FIG. 11E shows a field use aimer arm 1032 having unique fiducial 1033 marked thereon, and having been seated in calibration handle 828 serving as a calibration jig thereby to physically associate the field use aimer arm 1032 with the calibration handle serving as the calibration jig. The arrowed dashed-line from handle 828 to aimer arm 1032 represents a second transformation from the frame M of calibration fiducial 829 of calibration handle 828 to the frame $N_1$ of aimer arm 1032 that is imparted by unique fiducial 1033. FIG. 11E also shows a different field use aimer arm 1132 having unique fiducial 1133 marked thereon, and having been seated in (the same) calibration handle 828 serving as a calibration jig. The arrowed dashed-line from handle 828 to aimer arm 1132 represents a second transformation from the frame M of calibration fiducial 829 to the frame $N_2$ of aimer arm 1132 that is imparted by unique fiducial 1133. Additional second transformations $N_3$, $N_4$ . . . $N_n$ may be conducted in a similar manner for additional field use aimer arms. Calculations of the poses of the geometric entities in the frame of unique fiducial 1033, the frame of unique fiducial 1133, and the frame of any unique fiducials marked on successive field use aimer arms may be conducted based on the respective second transformations. The calculated poses may be electronically stored as geometric entity data in association with an identification of the unique fiducial to which they pertain—for example using an unique identifier associated with the respective field use aimer arm. Each field use aimer arm is dissociated from the calibration handle 828 serving as the calibration jig for use during a surgical navigation. At the time of the surgical procedure, a unique set of geometric entity data may be retrieved by or otherwise made available to the surgical controller for use with a tibial aimer that incorporates as a component the respective field use aimer arm for which the unique set of geometric entity data was generated. It will be appreciated that, certain surgical tools, such as tibial aimers, may be configured to assume multiple physical states, and that multiple poses of geometric entities corresponding to respective physical states may be carried by the unique fiducials 1033, 1133 and others like them.

FIG. 11F shows field use aimer arm 1032 having unique fiducial 1033 marked thereon, with poses of the geometric entities 934, 930A, 930B, 930C represented in the frame of calibration fiducial 829 on calibration handle 828 having been transferred to the frame of unique fiducial 1033, and represented as geometric entities 1034, 1030A, 1030B, 1030C. Unique fiducial 1033 may therefore be thought of as "carrying" the poses of the geometric entities 1034, 1030A, 1030B, 1030C. FIG. 11F also shows field use aimer arm 1132 having unique fiducial 1133 marked thereon, with poses of the geometric entities 934, 930A, 930B, 930C represented in the frame of calibration fiducial 829 on calibration handle 828 having been transferred to the frame of unique fiducial 1133, and represented as geometric entities 1134, 1130A, 1130B, 1130C. Unique fiducial 1133 may therefore be thought of as "carrying" the poses of the geometric entities 1134, 1130A, 1130B, 1130C. Each aimer arm 1032, 1132 and any other aimer arms calibration in the same manner may thereafter be physically associated for a surgical procedure with a respective field use handle, and used for tracking of the poses of the geometric entities in the surgical site.

Alternative methods for calibration involving a calibration jig are possible. For example, FIGS. 12A-12G show representations of another method in which a component of a field instrument that is affixed with a unique fiducial is calibrated using a calibration jig. In these figures, rather than transferring poses of geometric entities from the frame of a calibration aimer arm as imparted by a respective calibration fiducial to the frame of a handle as imparted by another respective calibration fiducial, a calibration aimer arm is assembled with a calibration handle to form a calibration tibial aimer. The calibration tibial aimer is thereafter registered to a digital model of the tibial aimer using a point pair method such as that described herein, or another method, to generate a transformation from the digital model of the tibial aimer to the calibration tibial aimer. Geometric entities in the frame of the digital model may thereafter be transferred based on the transformation from the digital model to the calibration tibial aimer, but associated with the calibration fiducial on the calibration handle. Thereafter, the geometric entity data carried by the calibration fiducial on the calibration handle serving as a calibration jig may be transferred to multiple field use aimer arms having respective unique fiducials marked thereon.

Figures 12A, 12B, 12C, 12D, 12E, 12F, 12G:
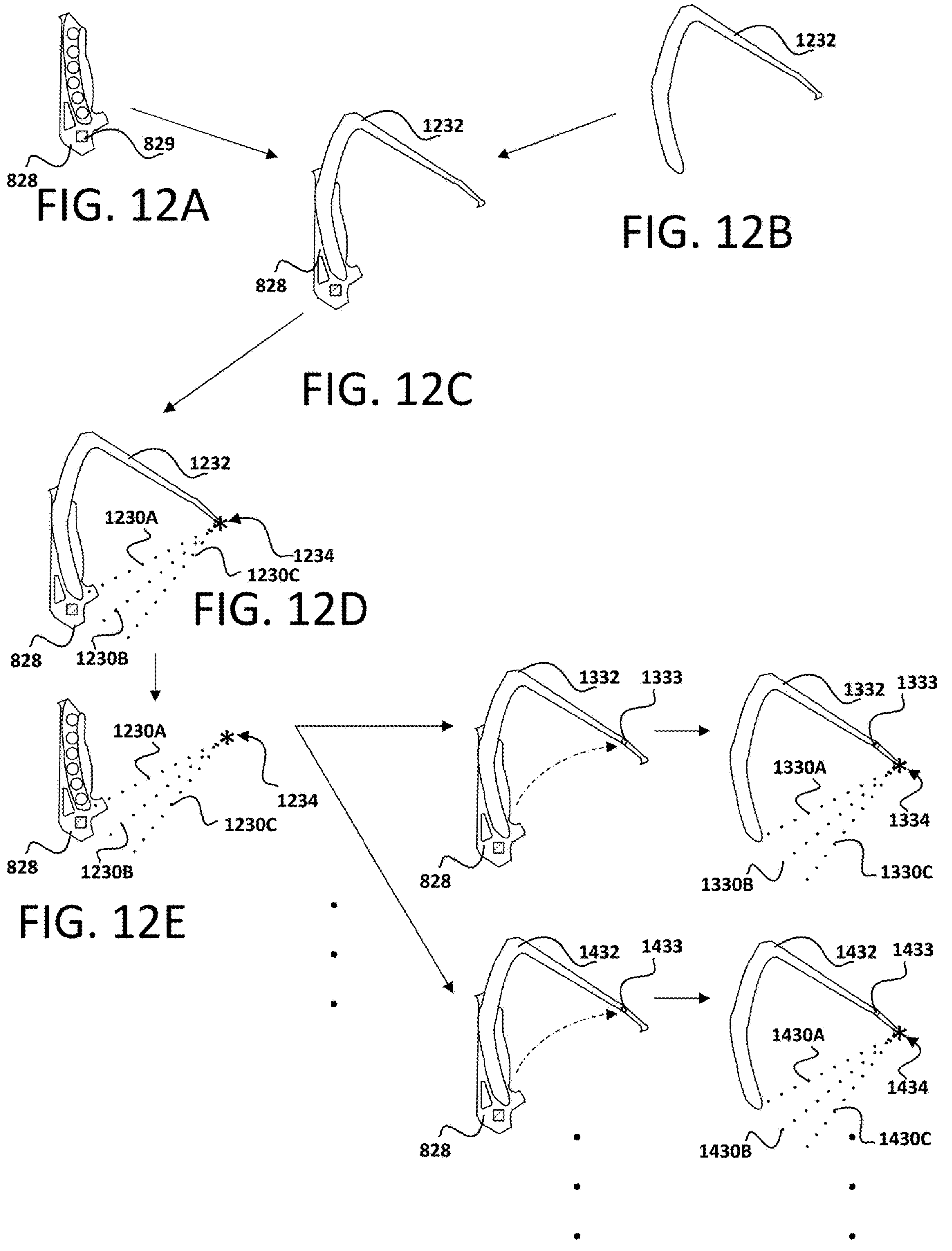
FIGS. 12A-12G show representations of another method in which a component of a field instrument that is affixed with a unique fiducial is calibrated using a calibration jig.

In particular, FIG. 12A shows a calibration handle 828 having a calibration fiducial 829 affixed to or marked thereon. Calibration handle 828 may be manufactured in accordance with a digital model of a surgical instrument, in this example of a tibial aimer. It will be appreciated that calibration handle 828 does not need, for the purpose of calibration of a field instrument or portion thereof, a bullet. FIG. 12B shows a calibration aimer arm 1232.

In FIG. 12C, calibration aimer arm 1232 is physically associated with handle 828, and seated within handle 828. A first transformation from a frame L of the digital model of the tibial aimer to a frame M of the calibration tibial aimer may be conducted by using a points pair method or other method as described herein. This particular transformation informs a transformation of the poses of geometric entities in the frame of the digital model to the frame of the calibration tibial aimer as imparted by calibration fiducial 829. FIG. 12D shows poses of geometric entities 1234, 1230A, 1230B, 1230C in the frame of calibration tibial aimer as imparted by calibration fiducial 829. The poses of geometric entities 1234, 1230A, 1230B, 1230C represented in the frame of calibration fiducial 829 may thereafter be transferred to multiple field user aimer arms.

FIG. 12E shows calibration fiducial 829 on handle 828 carrying the poses of geometric entities 1234, 1230A, 1230B, 1230C in the absence of calibration aimer arm 1232.

FIG. 12F shows a field use aimer arm 1332 having unique fiducial 1333 marked thereon, and having been seated in calibration handle 828 serving as a calibration jig thereby to physically associate the field use aimer arm 1332 with the calibration handle serving as the calibration jig. The arrowed dashed-line from handle 828 to aimer arm 1332 represents a second transformation from the frame M of calibration fiducial 829 of calibration handle 828 to the frame $N_1$ of aimer arm 1332 that is imparted by unique fiducial 1333. FIG. 12F also shows a different field use aimer arm 1432 having unique fiducial 1433 marked thereon, and having been seated in (the same) calibration handle 828 serving as a calibration jig. The arrowed dashed-line from handle 828 to aimer arm 1432 represents a second transformation from the frame M of calibration fiducial 829 to the frame $N_2$ of aimer arm 1432 that is imparted by unique fiducial 1433. Additional second transformations $N_3$, $N_4$ . . . . $N_n$ may be conducted in a similar manner for additional field use aimer arms. Calculations of the poses of the geometric entities in the frame of unique fiducial 1333, the frame of unique fiducial 1433, and the frame of any unique fiducials marked on successive field use aimer arms may be conducted based on the respective second transformations. The calculated poses may be electronically stored as geometric entity data in association with an identification of the unique fiducial to which they pertain—for example using an unique identifier associated with the respective field use aimer arm. Each field use aimer arm is dissociated from the calibration handle 828 serving as the calibration jig for use during a surgical navigation. At the time of the surgical procedure, a unique set of geometric entity data may be retrieved by or otherwise made available to the surgical controller for use with a tibial aimer that incorporates as a component the respective field use aimer arm for which the unique set of geometric entity data was generated. It will be appreciated that, certain surgical tools, such as tibial aimers, may be configured to assume multiple physical states, and that multiple poses of geometric entities corresponding to respective physical states may be carried by the unique fiducials 1333, 1433 and others like them.

FIG. 12G shows field use aimer arm 1332 having unique fiducial 1333 marked thereon, with poses of the geometric entities 1234, 1230A, 1230B, 1230C represented in the frame of calibration fiducial 829 on calibration handle 828 having been transferred to the frame of unique fiducial 1333, and represented as geometric entities 1334, 1330A, 1330B, 1330C. Unique fiducial 1333 may therefore be thought of as "carrying" the poses of the geometric entities 1334, 1330A, 1330B, 1330C. FIG. 12G also shows field use aimer arm 1432 having unique fiducial 1433 marked thereon, with poses of the geometric entities 1234, 1230A, 1230B, 1230C represented in the frame of calibration fiducial 829 on calibration handle 828 having been transferred to the frame of unique fiducial 1433, and represented as geometric entities 1434, 1430A, 1430B, 1430C. Unique fiducial 1433 may therefore be thought of as "carrying" the poses of the geometric entities 1434, 1430A, 1430B, 1430C. Each aimer arm 1332, 1432 and any other aimer arms calibration in the same manner may thereafter be physically associated for a surgical procedure with a respective field use handle, and used for tracking of the poses of the geometric entities in the surgical site.

At the time of a surgical procedure, in order to configure a surgical controller so that it may incorporate a field instrument into surgical guidance, the field instrument may be physically associated with an unique fiducial at the time of the surgical procedure. The unique fiducial may be received ready for assembly with a surgical tool in a package. The package may itself be marked with an identification of the unique fiducial. Such an identification may be a machine-readable code and/or may be a human readable code. The code is entered into the surgical controller either manually or with the aid of a scanner associated with the surgical controller. The surgical controller receives the identification of the unique fiducial and, using the identification, retrieves stored geometric entity data that may be stored in the form of a calibration file for the unique fiducial that specifies the unique calibration to the digital model of the surgical tool for the unique fiducial. Thereafter, while receiving a video stream of the surgical site, the surgical controller may process images of the video stream to detect and determine poses of the unique fiducial within the surgical site. Based on the poses of the unique fiducial within the surgical site and the stored geometric entity data, the surgical controller calculates one or more poses with respect to the surgical site of each geometric entity whose pose is represented in the geometric entity data. With the one or more poses of each geometric entity with respect to the surgical site having been calculated, the surgical controller can display, on a display device in association with the video stream, surgical navigation information based at least on the calculated poses. The surgical navigation information may comprise a visual representation of values calculated based on the calculated poses and/or may comprise a visual representation of the poses themselves. The stored geometric entity data may have been generated and stored during a calibration of the unique fiducial to a calibration instrument that physically corresponds to the field instrument as described herein, may have been generated and stored during a calibration of the unique fiducial to a digital model of the field instrument as described herein, or may have been generated and stored during a calibration conducted in some other manner. Where the surgical instrument can assume different physical states-such as in the case of a tibial aimer where the aimer arm can be moved with respect to the handle, and thus with respect to the bullet-communicating a current physical state of the surgical instrument to the surgical controller may be done in various ways. For example, position sensors on the surgical instrument may be used to automatically determine the physical state and to communicate the physical state electronically to the surgical instrument. Alternatively, a surgeon when adjusting the surgical instrument may manually enter into the surgical controller the current physical state, for example by reading a number from a scale on the surgical instrument. Variations and alternatives are possible. The surgical controller may receive an indication of the current physical state and select, from the stored geometric data for the purpose of the calculating, one of the multiple poses of a geometric entity that corresponds to the current physical state.

Figure 13:
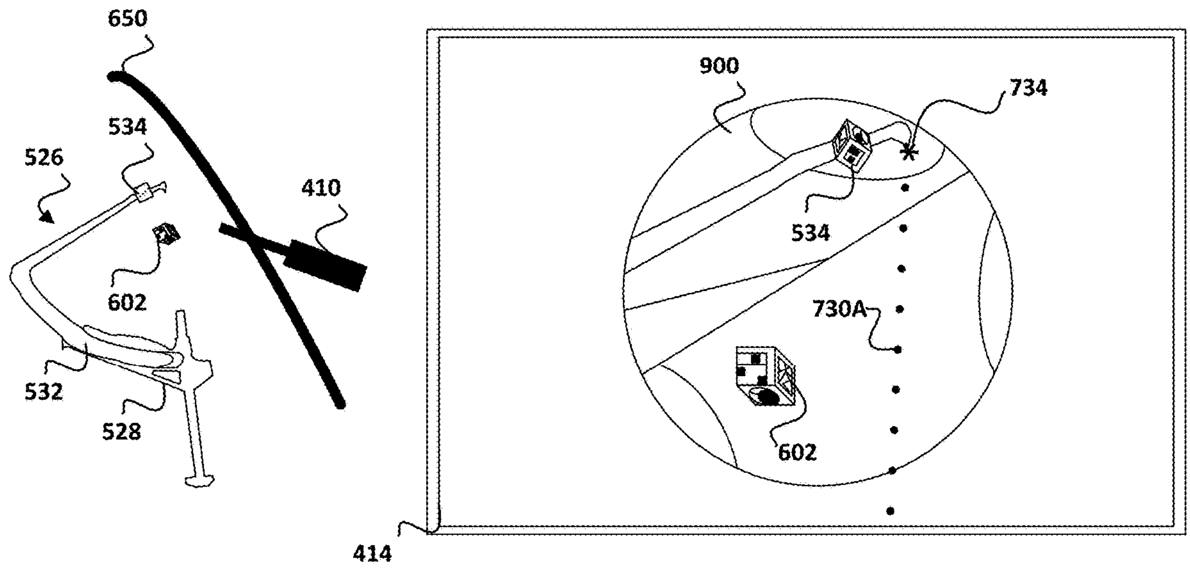
FIG. 13 shows a relative orientation of an arthroscopic camera with respect to a surgical site and a corresponding display on which a video frame captured by the arthroscopic camera is displayed along with surgical navigation information based on poses of geometric entities of a field instrument in the surgical site.

FIG. 13 shows display 414 with an arthroscopic view 900 of the surgical site, as seen within the field of view of arthroscope 408 and attached camera head 410. To the left of display 414 is a relational view of the position and orientation of instrument fiducial 534 of a surgical instrument (in this example, tibial aimer 526) with respect to a bone fiducial 602, as would be seen by camera head 410. This relational view is not that which would be displayed to a surgeon, as a surgeon would have instrument 526 in hand to manipulate in the surgical room. Rather, the relational view is shown in this figure to demonstrate how contents of display 414 may be presented depending on the position and orientation of instrument fiducial 534 with respect to bone fiducial 602. In particular, in this figure, a visual representation 730A of a geometric entity taking the form of a dotted line indicia corresponding to the axis through the bullet of the surgical instrument 526 is shown displayed on display 414, overlying arthroscopic view 900 but extending beyond it to the bottom as it extends beyond the field of view of camera head 410 through to the bullet itself. Also, a visual representation 734 of a geometric entity taking the form of an asterisk indicia at a point corresponding to the tip of the aimer arm of the surgical instrument is also displayed on display 414, overlying arthroscopic view 900. Only a central circular portion of display 414 is taken up with arthroscopic view 900. The poses (i.e., positions and orientations) of visual representations 730A and 734 are calculated in real-time or near real-time, or otherwise periodically, based on poses of instrument fiducial 534 with respect to bone fiducial 602, the physical state of tibial aimer 526 and the geometric entity data corresponding to instrument fiducial 534. It will be appreciated that, even though no part of the bullet of instrument 526 is visible in arthroscopic view 900 due to instrument 526 not being fully encompassed within the view of view of camera head 410, visual representation 730A may still be calculated and displayed in conjunction with the arthroscopic view 900 being displayed on display 414. Calculations may be based on camera head 410 capturing instrument fiducial 534 and bone fiducial 602, the images/frames of the captured video being processed to determine the relative position and orientation of instrument fiducial 534 in the internal frame or coordinate system corresponding to bone fiducial 602, the relative poses being provided in the geometric entity data, and the physical state of tibial aimer 526. With the guidance of visual representations 730A and 734, a surgeon may be able to determine how to position and orient instrument 526 so that it coincides with an intended position and orientation with respect to, for example, the bone model.

Figure 14:
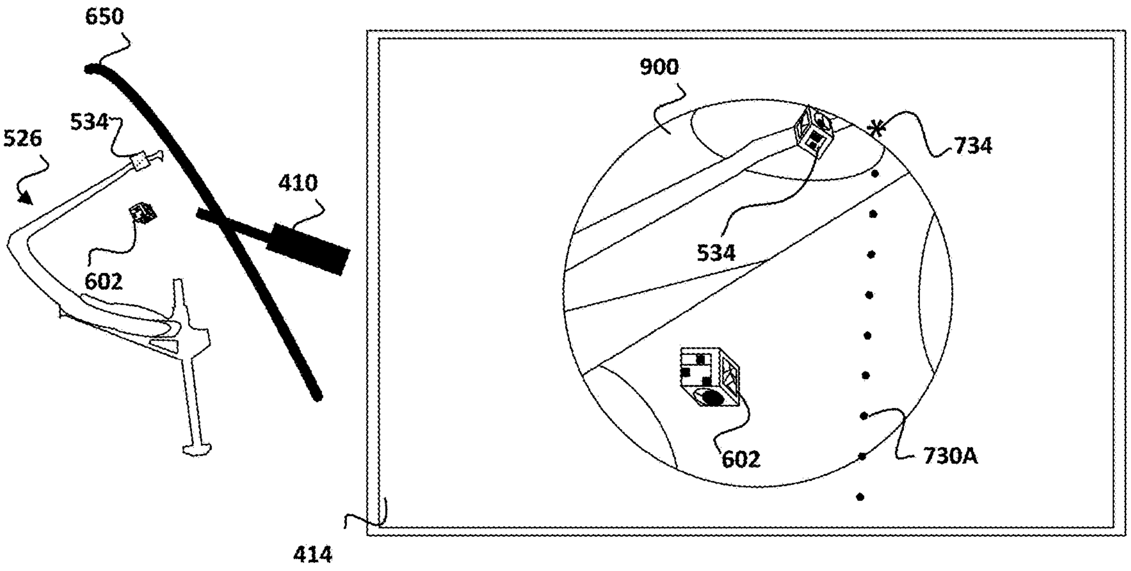
FIG. 14 shows a different relative orientation of an arthroscopic camera with respect to a surgical site and a corresponding display on which a video frame captured by the arthroscopic camera is displayed along with surgical navigation information based on poses of geometric entities of a field instrument in the surgical site.

FIG. 14 shows display 414 with an arthroscopic view 900 of the surgical site, as seen within the field of view of arthroscope 408 and attached camera head 410. To the left of display 414 is a relational view of the position and orientation of instrument fiducial 534 with respect to a bone fiducial 602, as would be seen by camera head 410. It will be noted that the instrument 526 has been moved slightly with respect to bone fiducial 602 and camera head 410. In this figure, a visual representation 730A of the dotted line indicia corresponding to the axis through the bullet of the surgical instrument 526 is shown displayed on display 414, overlying arthroscopic view 900 but extending beyond it to both the top and the bottom as it extends beyond the field of view of the camera head 410 from the bullet itself through to the tip of the aimer arm. Because of the slight movement of instrument 526, the visual representation 734 of the asterisk indicia corresponding to the tip of the aimer arm of the surgical instrument is also moved so that it no longer overlies arthroscopic view 900. That is, since the tip of the instrument 526 is not within the field of view of camera head 410, visual representation 734—the asterisk—corresponding to the tip is shown only outside of arthroscopic view 900 but is still visible on display 414 since only a central circular portion of display 414 is taken up with arthroscopic view 900. It will be appreciated that, even though no part of the bullet of instrument 526 is visible in arthroscopic view 900 due to instrument 526 not being fully encompassed within the view of view of arthroscope 408 and attached camera head 410, visual representation 730A may be calculated and displayed in conjunction with the arthroscopic view 900 being displayed on display 414. Similarly, even though the tip of instrument 526 is not visible in arthroscopic view 900, visual representation 734 may be calculated and displayed in conjunction with the arthroscopic view 900 being displayed on display 414. Even with these components of instrument 526 not being within the field of view of camera head 410, due to fiducials 534 and 602, such visual indications may be generated and displayed. Again, with the guidance of visual representations 734 and 730A, a surgeon may be able to determine how to position and orient instrument 526 so that it coincides with an intended position and orientation with respect to, for example, the bone model.

Other forms of visual representation may be displayed in conjunction with or in lieu of visual representations of the poses themselves such as the line and point of visual representations 730A, 734. For example, a visual representation of values calculated based on the poses with respect to the surgical site may be displayed on display 414 in association with the display of the images of the video stream captured by camera head 410. Such values may include angle values or trajectory values of the bullet axis with respect to the surgical site, values indicative of the alignment with or proximity of the bullet axis with respect to a planned tunnel path, or other such values.

Software and Hardware

Figure 15:
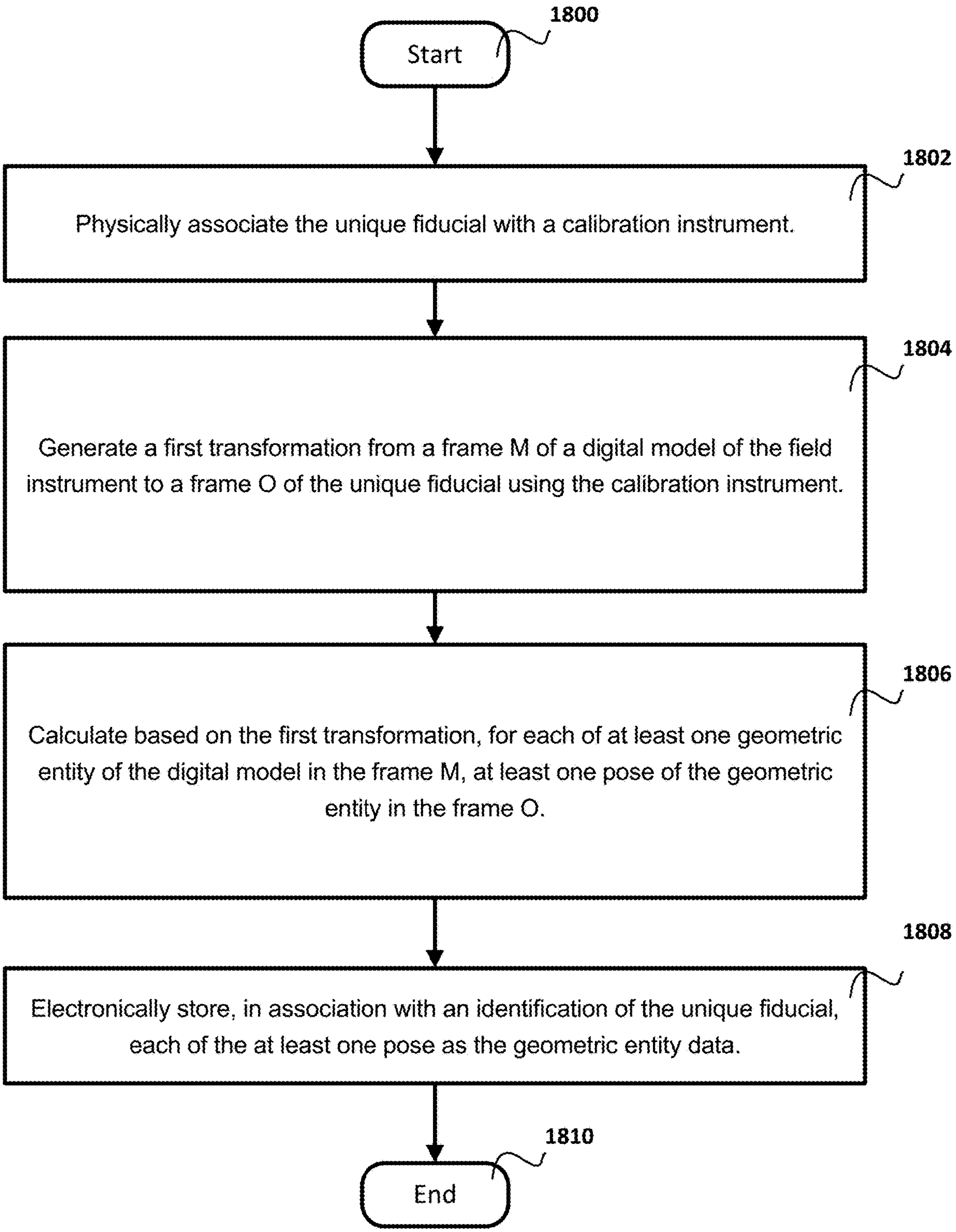
FIG. 15 shows a method of generating, for a unique fiducial, geometric entity data corresponding to a field instrument, in accordance with at least some embodiments.

FIG. 15 shows a method of generating, for a unique fiducial, geometric entity data corresponding to a field instrument, in accordance with at least some embodiments. In particular, the method starts (block 1800) and comprises: physically associating the unique fiducial with a calibration instrument (block 1802); generating a first transformation from a frame M of a digital model of the field instrument to a frame O of the unique fiducial using the calibration instrument (block 1804); calculating based on the first transformation, for each of at least one geometric entity of the digital model in the frame M, at least one pose of the geometric entity in the frame O (block 1806); and electronically storing, in association with an identification of the unique fiducial, each of the at least one pose as the geometric entity data (block 1808). Thereafter, the method ends (block 1810). The unique fiducial is physically dissociated from the calibration instrument to be physically associated with the field instrument for use in a video-based surgical navigation. The example method may be implemented by computer instructions executed with the processor of computer system, such as the surgical controller 418 (FIG. 4).

Figure 16:
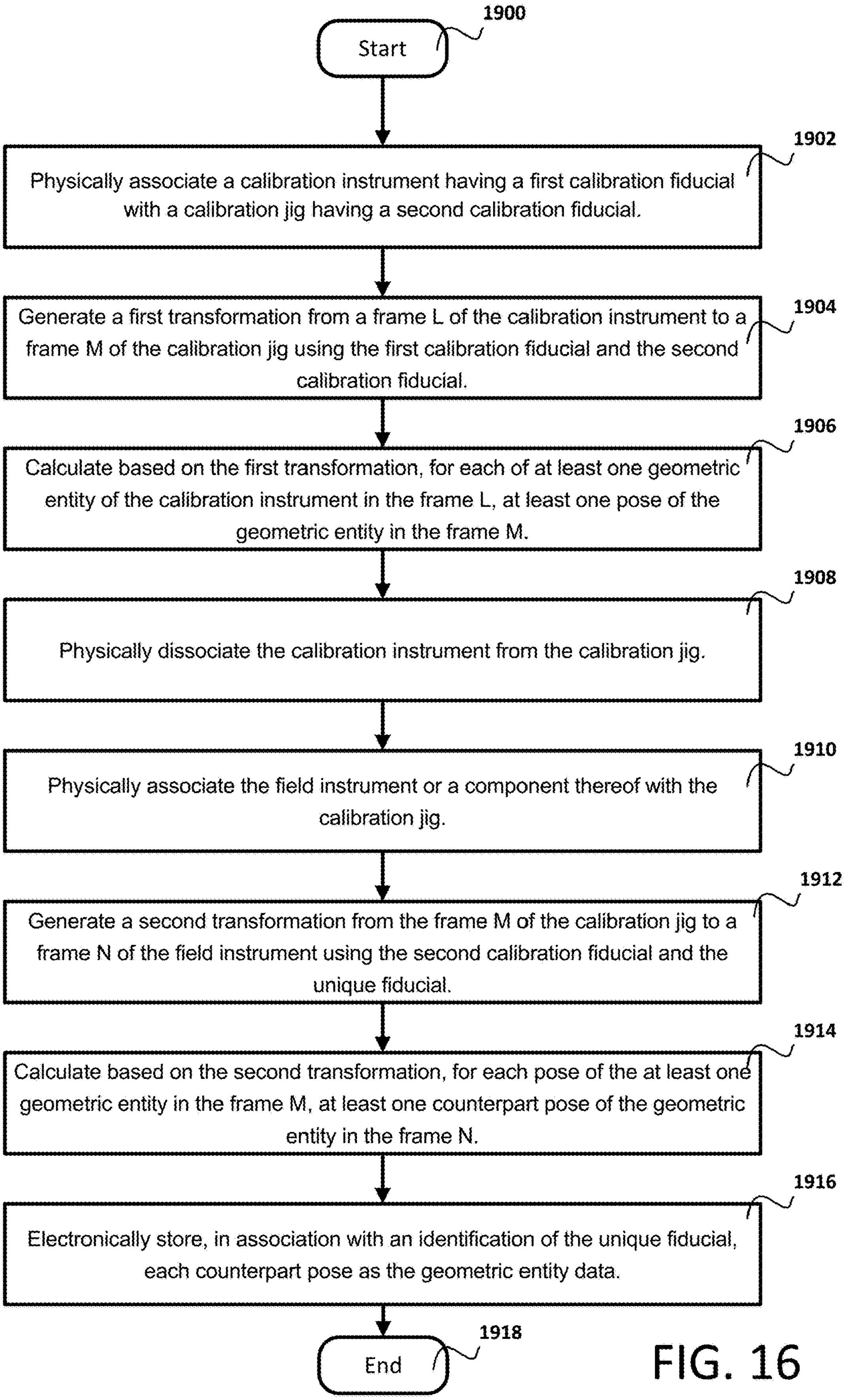
FIG. 16 shows a method of generating geometric entity data for a field instrument having a unique fiducial, in accordance with at least some embodiments.

FIG. 16 shows a method of generating geometric entity data for a field instrument having a unique fiducial, in accordance with at least some embodiments. In particular, the method starts (block 1900) and comprises: physically associating a calibration instrument having a first calibration fiducial with a calibration jig having a second calibration fiducial (block 1902); generating a first transformation from a frame L of the calibration instrument to a frame M of the calibration jig using the first calibration fiducial and the second calibration fiducial (block 1904); calculating based on the first transformation, for each of at least one geometric entity of the calibration instrument in the frame L, at least one pose of the geometric entity in the frame M (block 1906); physically dissociating the calibration instrument from the calibration jig (block 1908); physically associating the field instrument or a component thereof with the calibration jig (block 1910); generating a second transformation from the frame M of the calibration jig to a frame N of the field instrument using the second calibration fiducial and the unique fiducial (block 1912); calculating based on the second transformation, for each pose of the at least one geometric entity in the frame M, at least one counterpart pose of the geometric entity in the frame N (block 1914); and electronically storing, in association with an identification of the unique fiducial, each counterpart pose as the geometric entity data (block 1916). Thereafter, the method ends (block 1918). The field instrument or the component thereof is physically dissociated from the calibration jig for use in a video-based surgical navigation.

Figure 17:
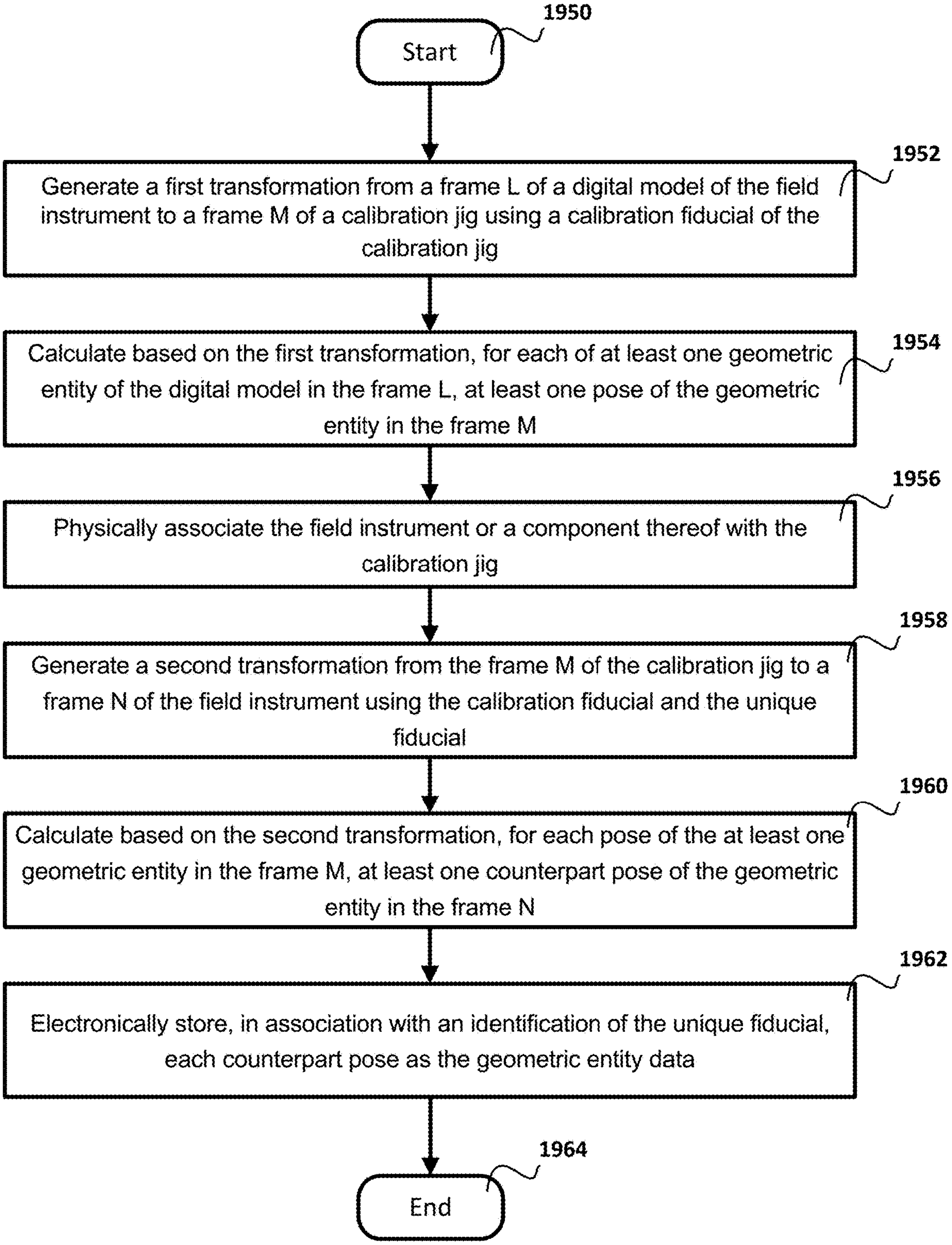
FIG. 17 shows a method of generating geometric entity data for a field instrument having a unique fiducial, in accordance with at least some embodiments.

FIG. 17 shows a method of generating geometric entity data for a field instrument having a unique fiducial, in accordance with at least some embodiments. In particular, the method starts (block 1950) and comprises: generating a first transformation from a frame L of a digital model of the field instrument to a frame M of a calibration jig using a calibration fiducial of the calibration jig (block 1952); calculating based on the first transformation, for each of at least one geometric entity of the digital model in the frame L, at least one pose of the geometric entity in the frame M (block 1954); physically associating the field instrument or a component thereof with the calibration jig (block 1956); generating a second transformation from the frame M of the calibration jig to a frame N of the field instrument using the calibration fiducial and the unique fiducial (block 1958); calculating based on the second transformation, for each pose of the at least one geometric entity in the frame M, at least one counterpart pose of the geometric entity in the frame N (block 1960); and electronically storing, in association with an identification of the unique fiducial, each counterpart pose as the geometric entity data (block 1962). Thereafter, the method ends (block 1964). The field instrument or the component thereof is physically dissociated from the calibration jig for use in a video-based surgical navigation.

Figure 18:
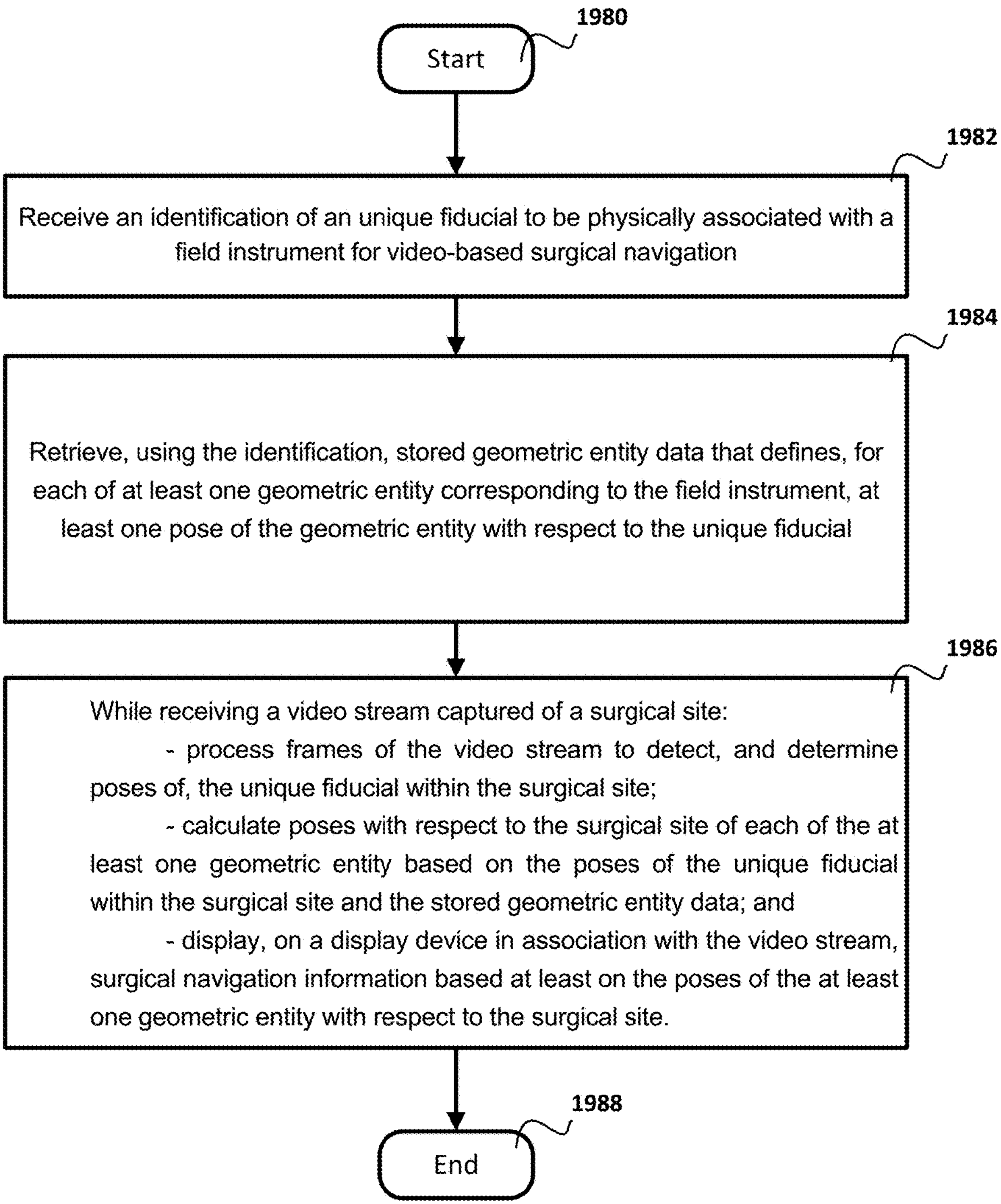
FIG. 18 shows a method conducted by a surgical controller, in accordance with at least some embodiments.

FIG. 18 shows a method conducted by a surgical controller, in accordance with at least some embodiments. In particular, the method starts (block 1980) and comprises: receiving an identification of an unique fiducial to be physically associated with a field instrument for video-based surgical navigation (block 1982); retrieving, using the identification, stored geometric entity data that defines, for each of at least one geometric entity corresponding to the field instrument, at least one pose of the geometric entity with respect to the unique fiducial (block 1984); and while receiving a video stream captured of a surgical site: processing frames of the video stream to detect, and determine poses of, the unique fiducial within the surgical site; calculating poses with respect to the surgical site of each of the at least one geometric entity based on the poses of the unique fiducial within the surgical site and the stored geometric entity data; and displaying, on a display device in association with the video stream, surgical navigation information based at least on the poses of the at least one geometric entity with respect to the surgical site (block 1986). Thereafter, the method ends (block 1988).

Figure 19:
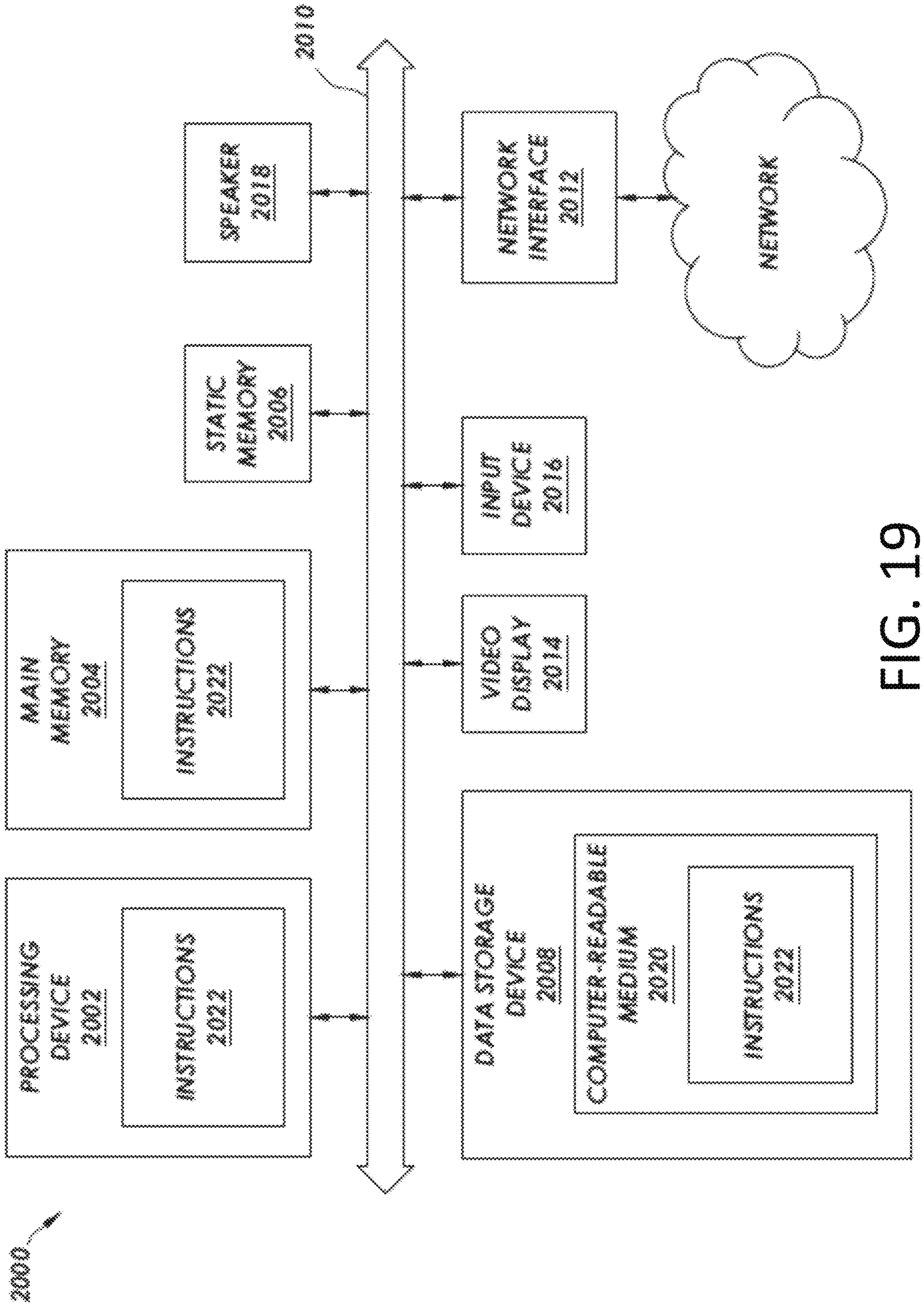
FIG. 19 shows a computer system in accordance with at least some embodiments.

FIG. 19 shows an example computer system 2000. In one example, computer system 2000 may correspond to the surgical controller 418, a tablet device within the surgical room, or any other system that implements any or all the various methods discussed in this specification as part of a surgical system. The computer system 2000 may be connected (e.g., networked) to other computer systems in a local-area network (LAN), an intranet, and/or an extranet (e.g., device cart 402 network), or at certain times the Internet (e.g., when not in use in a surgical procedure). The computer system 2000 may be a server, a personal computer (PC), a tablet computer or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 2000 includes a processing device 2002, a main memory 2004 (e.g., read-only memory (ROM), flash memory, dynamic random access memory (DRAM) such as synchronous DRAM (SDRAM)), a static memory 2006 (e.g., flash memory, static random access memory (SRAM)), and a data storage device 2008, which communicate with each other via a bus 2010.

Processing device 2002 represents one or more general-purpose processing devices such as a microprocessor, central processing unit, or the like. More particularly, the processing device 2002 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 2002 may also be one or more special-purpose processing devices such as an application specific integrated circuit (ASIC), a field programmable gate array (FPGA), a digital signal processor (DSP), network processor, or the like. The processing device 2002 is configured to execute instructions for performing any of the operations and steps discussed herein. Once programmed with specific instructions, the processing device 2002, and thus the entire computer system 2000, becomes a special-purpose device, such as the surgical controller 418.

The computer system 2000 may further include a network interface device 2012 for communicating with any suitable network (e.g., the device cart 402 network). The computer system 2000 also may include a video display 2014 (e.g., display device 414), one or more input devices 2016 (e.g., a microphone, a keyboard, and/or a mouse), and one or more speakers 2018. In one illustrative example, the video display 2014 and the input device(s) 2016 may be combined into a single component or device (e.g., an LCD touch screen).

The data storage device 2008 may include a computer-readable storage medium 2020 on which the instructions 2022 (e.g., implementing any methods and any functions performed by any device and/or component depicted described herein) embodying any one or more of the methodologies or functions described herein is stored. The instructions 2022 may also reside, completely or at least partially, within the main memory 2004 and/or within the processing device 2002 during execution thereof by the computer system 2000. As such, the main memory 2004 and the processing device 2002 also constitute computer-readable media. In certain cases, the instructions 2022 may further be transmitted or received over a network via the network interface device 2012.

While the computer-readable storage medium 2020 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

While various embodiments have been described, alternatives are possible.

For example, if the physical substrate for a fiducial can be machined to low error tolerance, a calibration of the fiducial markings made on the physical substrate for the fiducial may be conducted. A known relationship between the physical substrate for the fiducial and the field use surgical instrument may thereafter be used to calculate a transformation between the unique fiducial markings and the surgical instrument. It will be appreciated that the physical substrate itself would be required to have features enabling it to be uniquely recognized in digital images thereby to transfer the transformation as between the fiducial markings and the surgical tool. This may limit the range of physical form factors available for such physical substrates.

Furthermore, while in examples described and depicted, a calibration handle having the physical form of a tibial aimer handle is used as a jig for an aimer arm during calibration, alternatives are possible. For example, a different physical form of jig—one that may not look like a tibial aimer handle, or that may not perhaps look like the exact tibial aimer handle with which the aimer arm will eventually be coupled for field use—for receiving, as well as reliably and repeatably engaging, a field use aimer arm for its calibration may be used. As another example, a different physical form of jig for receiving a whole assembly of a field instrument tibial aimer—including, for example, the field use tibial aimer handle that is, in turn, receiving the field use tibial aimer arm with which it will be deployed for field use—may be used for calibration in a similar manner as has been described herein. Also, it will be appreciated that, where other kinds (formats; shapes) of field instruments or components thereof than tibial aimers are being calibrated in accordance with the principles explained herein, a corresponding jig will have a physical format that corresponds to (i.e. can receive and reliably and repeatably engage) the respective kind of field instrument or component thereof to be calibrated.

CLAUSES

Clause 1. A method of generating, for a unique fiducial, geometric entity data corresponding to a field instrument, the method comprising:

- physically associating the unique fiducial with a calibration instrument;
- generating a first transformation from a frame M of a digital model of the field instrument to a frame O of the unique fiducial using the calibration instrument;
- calculating based on the first transformation, for each of at least one geometric entity of the digital model in the frame M, at least one pose of the geometric entity in the frame O; and
  - electronically storing, in association with an identification of the unique fiducial, each of the at least one pose as the geometric entity data,
  - wherein the unique fiducial is physically dissociated from the calibration instrument to be physically associated with the field instrument for use in a video-based surgical navigation.

Clause 2. The method of clause 1, wherein generating the first transformation comprises:

- registering each of a plurality of locations along the digital model of the field instrument to a counterpart location along the calibration instrument.

Clause 3. The method of clause 1, wherein a calibration fiducial is physically associated with the calibration instrument and a first intermediate transformation from the frame M to a frame O' of the calibration fiducial has been generated using the calibration instrument, and wherein generating the first transformation comprises:

- generating a second intermediate transformation from the frame O' to the frame O, wherein the first transformation is a combination of the first intermediate transformation and the second intermediate transformation.

Clause 4. The method of clause 3, wherein generating the second intermediate transformation from the frame O' to the frame O comprises:

- capturing at least one digital image containing both the unique fiducial and the calibration fiducial; and
- processing the at least one digital image to generate the second intermediate transformation.

Clause 5. The method of clause 1, wherein the field instrument can be configured to assume multiple physical states, wherein the calculating comprises:

- calculating based on the first transformation, for at least one of the at least one geometric entity of the digital model in the frame M, poses of the geometric entity in the frame O, wherein each of the poses corresponds to a respective one of the physical states.

Clause 6. The method of clause 5, wherein the field instrument is a tibial aimer having an aimer arm and a handle, and wherein the physical states are positions of the aimer arm with respect to the handle.

Clause 7. The method of clause 6, wherein the geometric entity data defines, for a line representing an axis of a bullet of the tibial aimer, multiple poses of the line with respect to the unique fiducial, each of the poses of the line corresponding to a respective position of the aimer arm with respect to the handle.

Clause 8. The method of clause 7, wherein the geometric entity data defines a point representing a location of a tip of the aimer arm.

Clause 9. A method of generating geometric entity data for a field instrument having a unique fiducial, the method comprising:

- physically associating a calibration instrument having a first calibration fiducial with a calibration jig having a second calibration fiducial;
- generating a first transformation from a frame L of the calibration instrument to a frame M of the calibration jig using the first calibration fiducial and the second calibration fiducial;
- calculating based on the first transformation, for each of at least one geometric entity of the calibration instrument in the frame L, at least one pose of the geometric entity in the frame M;
- physically dissociating the calibration instrument from the calibration jig;
- physically associating the field instrument or a component thereof with the calibration jig;
- generating a second transformation from the frame M of the calibration jig to a frame N of the field instrument using the second calibration fiducial and the unique fiducial;
- calculating based on the second transformation, for each pose of the at least one geometric entity in the frame M, at least one counterpart pose of the geometric entity in the frame N; and
  - electronically storing, in association with an identification of the unique fiducial, each counterpart pose as the geometric entity data,
- wherein the field instrument or the component thereof is physically dissociated from the calibration jig for use in a video-based surgical navigation.

Clause 10. The method of clause 9,

- wherein the field instrument can be configured to assume multiple physical states,
- wherein the calculating based on the first transformation comprises calculating, for at least one of the at least one geometric entity of the calibration instrument in the frame L, poses of the geometric entity in the frame M, wherein each of the poses corresponds to a respective one of the physical states, wherein the calculating based on the second transformation comprises calculating, for the poses of the geometric entity in the frame M, counterpart poses of the geometric entity in the frame N.

Clause 11. The method of clause 10, wherein the field instrument is a tibial aimer having an aimer arm and a handle, and wherein the physical states are positions of the aimer arm with respect to the handle.

Clause 12. The method of clause 11, wherein the geometric entity data defines, for a line representing an axis of a bullet of the tibial aimer, multiple poses of the line with respect to the unique fiducial, each of the poses of the line corresponding to a respective position of the aimer arm with respect to the handle.

Clause 13. The method of clause 12, wherein the geometric entity data defines a point representing a location of a tip of the aimer arm.

Clause 14. A method of generating geometric entity data for a field instrument having a unique fiducial, the method comprising:

generating a first transformation from a frame L of a digital model of the field instrument to a frame M of a calibration jig using a calibration fiducial of the calibration jig;

calculating based on the first transformation, for each of at least one geometric entity of the digital model in the frame L, at least one pose of the geometric entity in the frame M;

physically associating the field instrument or a component thereof with the calibration jig;

generating a second transformation from the frame M of the calibration jig to a frame N of the field instrument using the calibration fiducial and the unique fiducial;

calculating based on the second transformation, for each pose of the at least one geometric entity in the frame M, at least one counterpart pose of the geometric entity in the frame N; and electronically storing, in association with an identification of the unique fiducial, each counterpart pose as the geometric entity data, wherein the field instrument or the component thereof is physically dissociated from the calibration jig for use in a video-based surgical navigation.

Clause 15. The method of clause 14, wherein the field instrument can be configured to assume multiple physical states, wherein the calculating based on the first transformation comprises calculating, for at least one of the at least one geometric entity of the digital model in the frame L, poses of the geometric entity in the frame M, wherein each of the poses corresponds to a respective one of the physical states, and wherein the calculating based on the second transformation comprises calculating, for the poses of the geometric entity in the frame M, counterpart poses of the geometric entity in the frame N.

Clause 16. The method of clause 15, wherein the field instrument is a tibial aimer having an aimer arm and a handle, and wherein the physical states are positions of the aimer arm with respect to the handle.

Clause 17. The method of clause 16, wherein the geometric entity data defines, for a line representing an axis of a bullet of the tibial aimer, multiple poses of the line with respect to the unique fiducial, each of the poses of the line corresponding to a respective position of the aimer arm with respect to the handle.

Clause 18. The method of clause 17, wherein the geometric entity data defines a point representing a location of a tip of the aimer arm.

Clause 19. A method conducted by a surgical controller comprising:

receiving an identification of an unique fiducial to be physically associated with a field instrument for video-based surgical navigation;

retrieving, using the identification, stored geometric entity data that defines, for each of at least one geometric entity corresponding to the field instrument, at least one pose of the geometric entity with respect to the unique fiducial; and while receiving a video stream captured of a surgical site:

processing images of the video stream to detect, and determine poses of, the unique fiducial within the surgical site;

calculating poses with respect to the surgical site of each of the at least one geometric entity based on the poses of the unique fiducial within the surgical site and the stored geometric entity data; and displaying, on a display device in association with the video stream, surgical navigation information based at least on the poses of the at least one geometric entity with respect to the surgical site.

Clause 20. The method of clause 19, wherein the surgical navigation information comprises a visual representation of the poses with respect to the surgical site of each of the at least one geometric entity.

Clause 21. The method of clause 19, wherein the surgical navigation information comprises a visual representation of values calculated based on the poses with respect to the surgical site of each of the at least one geometric entity.

Clause 22. The method of clause 19, wherein the stored geometric entity data was generated and stored during a calibration of the unique fiducial to a digital model of the field instrument.

Clause 23. The method of clause 19, wherein the stored geometric entity data was generated and stored during a calibration of the unique fiducial to a calibration instrument that physically corresponds to the field instrument.

Clause 24. The method of clause 19, wherein each of the at least one geometric entity is selected from the group consisting of: a point, a line, and a plane.

Clause 25. The method of clause 19, wherein the field instrument is a tibial aimer, and the at least one geometric entity comprises:

a first geometric entity that is a point to correspond to a location of a tip of the tibial aimer; and a second geometric entity that is a line to correspond to an axis of a bullet of the tibial aimer.

Clause 26. The method of clause 19, wherein the stored geometric entity data defines, for at least one of the at least one geometric entity, multiple poses of the geometric entity with respect to the unique fiducial each corresponding to a respective physical state of the field instrument.

Clause 27. The method of clause 26, further comprising:

receiving an indication of a current physical state of the field instrument; and selecting, from the stored geometric entity data for the calculating, one of the multiple poses of the geometric entity that corresponds to the current physical state.

Clause 28. The method of clause 26, wherein the field instrument is a tibial aimer having an aimer arm component and a handle component, and wherein each physical state is a position of the aimer arm component with respect to the handle component.

Clause 29. The method of clause 28, wherein the stored geometric entity data defines, for a line representing an axis of a bullet of the tibial aimer, multiple poses of the line with respect to the unique fiducial, each of the poses of the line corresponding to the position of the aimer arm component with respect to the handle component.

Clause 30. The method of clause 29, wherein the stored geometric entity data defines a point representing a location of a tip of the aimer arm component.

Clause 31. A surgical controller comprising:

processing structure comprising at least one computer processor, the processing structure in communication with a display device; and a memory coupled to the processing structure and storing instructions that, when executed by the processing structure, cause the processing structure to:

receive an identification of an unique fiducial to be physically associated with a field instrument for video-based surgical navigation;

retrieve, using the identification, stored geometric entity data that defines, for each of at least one geometric entity corresponding to the field instrument, at least one pose of the geometric entity with respect to the unique fiducial; and while receiving a video stream captured of a surgical site:

process images of the video stream to detect, and determine poses of, the unique fiducial within the surgical site;

calculate poses with respect to the surgical site of each of the at least one geometric entity based on the poses of the unique fiducial within the surgical site and the stored geometric entity data; and display, on the display device in association with the video stream, surgical navigation information based at least on the poses of the at least one geometric entity with respect to the surgical site.

Clause 32. The surgical controller of clause 31, wherein the surgical navigation information comprises a visual representation of the poses with respect to the surgical site of each of the at least one geometric entity.

Clause 33. The surgical controller of clause 31, wherein the surgical navigation information comprises a visual representation of values calculated based on the poses with respect to the surgical site of each of the at least one geometric entity.

Clause 34. The surgical controller of clause 31, wherein the stored geometric entity data was generated and stored during a calibration of the unique fiducial to a digital model of the field instrument.

Clause 35. The surgical controller of clause 31, wherein the stored geometric entity data was generated and stored during a calibration of the unique fiducial to a calibration instrument that physically corresponds to the field instrument.

Clause 36. The surgical controller of clause 31, wherein each of the at least one geometric entity is selected from the group consisting of: a point, a line, and a plane.

Clause 37. The surgical controller of clause 31, wherein the field instrument is a tibial aimer, and the at least one geometric entity comprises:

a first geometric entity that is a point to correspond to a location of a tip of the tibial aimer; and a second geometric entity that is a line to correspond to an axis of a bullet of the tibial aimer.

Clause 38. The surgical controller of clause 31, wherein the stored geometric entity data defines, for at least one of the at least one geometric entity, multiple poses of the geometric entity with respect to the unique fiducial each corresponding to a respective physical state of the field instrument.

Clause 39. The surgical controller of clause 38, wherein the instructions further cause the processing structure to:

receive an indication of a current physical state of the field instrument; and select, from the stored geometric entity data to calculate, one of the multiple poses of the geometric entity that corresponds to the current physical state.

Clause 40. The surgical controller of clause 38, wherein the field instrument is a tibial aimer having an aimer arm component and a handle component, and wherein each physical state is a position of the aimer arm component with respect to the handle component.

Clause 41. The surgical controller of clause 40, wherein the stored geometric entity data defines, for a line representing an axis of a bullet of the tibial aimer, multiple poses of the line with respect to the unique fiducial, each of the poses of the line corresponding to a respective position of the aimer arm component with respect to the handle component.

Clause 42. The surgical controller of clause 41, wherein the stored geometric entity data defines a point representing a location of a tip of the aimer arm component.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method of generating, for a unique fiducial, geometric entity data corresponding to a field instrument, the method comprising:

physically associating the unique fiducial with a calibration instrument;

generating a first transformation from a frame M of a digital model of the field instrument to a frame O of the unique fiducial using the calibration instrument;

calculating based on the first transformation, for each of at least one geometric entity of the digital model in the frame M, at least one pose of the geometric entity in the frame O; and electronically storing, in association with an identification of the unique fiducial, each of the at least one pose as the geometric entity data, wherein the unique fiducial is physically dissociated from the calibration instrument to be physically associated with the field instrument for use in a video-based surgical navigation.

2. The method of claim 1, wherein generating the first transformation comprises:

registering each of a plurality of locations along the digital model of the field instrument to a counterpart location along the calibration instrument.

3. The method of claim 1, wherein a calibration fiducial is physically associated with the calibration instrument and a first intermediate transformation from the frame M to a frame O' of the calibration fiducial has been generated using the calibration instrument, and wherein generating the first transformation comprises:

generating a second intermediate transformation from the frame O' to the frame O, wherein the first transformation is a combination of the first intermediate transformation and the second intermediate transformation.

4. The method of claim 3, wherein generating the second intermediate transformation from the frame O' to the frame O comprises:

capturing at least one digital image containing both the unique fiducial and the calibration fiducial; and processing the at least one digital image to generate the second intermediate transformation.

5. The method of claim 1, wherein the field instrument can be configured to assume multiple physical states, wherein the calculating comprises:

calculating based on the first transformation, for at least one of the at least one geometric entity of the digital model in the frame M, poses of the geometric entity in the frame O, wherein each of the poses corresponds to a respective one of the physical states.

6. The method of claim 5, wherein the field instrument is a tibial aimer having an aimer arm and a handle, and wherein the physical states are positions of the aimer arm with respect to the handle.

7. The method of claim 6, wherein the geometric entity data defines, for a line representing an axis of a bullet of the tibial aimer, multiple poses of the line with respect to the unique fiducial, each of the poses of the line corresponding to a respective position of the aimer arm with respect to the handle.

8. The method of claim 7, wherein the geometric entity data defines a point representing a location of a tip of the aimer arm.

9. A method of generating geometric entity data for a field instrument having a unique fiducial, the method comprising:

physically associating a calibration instrument having a first calibration fiducial with a calibration jig having a second calibration fiducial;

generating a first transformation from a frame L of the calibration instrument to a frame M of the calibration jig using the first calibration fiducial and the second calibration fiducial;

calculating based on the first transformation, for each of at least one geometric entity of the calibration instrument in the frame L, at least one pose of the geometric entity in the frame M;

physically dissociating the calibration instrument from the calibration jig;

physically associating the field instrument or a component thereof with the calibration jig;

generating a second transformation from the frame M of the calibration jig to a frame N of the field instrument using the second calibration fiducial and the unique fiducial;

calculating based on the second transformation, for each pose of the at least one geometric entity in the frame M, at least one counterpart pose of the geometric entity in the frame N; and electronically storing, in association with an identification of the unique fiducial, each counterpart pose as the geometric entity data, wherein the field instrument or the component thereof is physically dissociated from the calibration jig for use in a video-based surgical navigation.

10. The method of claim 9, wherein the field instrument can be configured to assume multiple physical states, wherein the calculating based on the first transformation comprises calculating, for at least one of the at least one geometric entity of the calibration instrument in the frame L, poses of the geometric entity in the frame M, wherein each of the poses corresponds to a respective one of the physical states, wherein the calculating based on the second transformation comprises calculating, for the poses of the geometric entity in the frame M, counterpart poses of the geometric entity in the frame N.

11. The method of claim 10, wherein the field instrument is a tibial aimer having an aimer arm and a handle, and wherein the physical states are positions of the aimer arm with respect to the handle.

12. The method of claim 11, wherein the geometric entity data defines, for a line representing an axis of a bullet of the tibial aimer, multiple poses of the line with respect to the unique fiducial, each of the poses of the line corresponding to a respective position of the aimer arm with respect to the handle.

13. The method of claim 12, wherein the geometric entity data defines a point representing a location of a tip of the aimer arm.

14. A method of generating geometric entity data for a field instrument having a unique fiducial, the method comprising:

generating a first transformation from a frame L of a digital model of the field instrument to a frame M of a calibration jig using a calibration fiducial of the calibration jig;

calculating based on the first transformation, for each of at least one geometric entity of the digital model in the frame L, at least one pose of the geometric entity in the frame M;

physically associating the field instrument or a component thereof with the calibration jig;

generating a second transformation from the frame M of the calibration jig to a frame N of the field instrument using the calibration fiducial and the unique fiducial;

calculating based on the second transformation, for each pose of the at least one geometric entity in the frame M, at least one counterpart pose of the geometric entity in the frame N; and electronically storing, in association with an identification of the unique fiducial, each counterpart pose as the geometric entity data, wherein the field instrument or the component thereof is physically dissociated from the calibration jig for use in a video-based surgical navigation.

15. The method of claim 14, wherein the field instrument can be configured to assume multiple physical states, wherein the calculating based on the first transformation comprises calculating, for at least one of the at least one geometric entity of the digital model in the frame L, poses of the geometric entity in the frame M, wherein each of the poses corresponds to a respective one of the physical states, and wherein the calculating based on the second transformation comprises calculating, for the poses of the geometric entity in the frame M, counterpart poses of the geometric entity in the frame N.

16. The method of claim 15, wherein the field instrument is a tibial aimer having an aimer arm and a handle, and wherein the physical states are positions of the aimer arm with respect to the handle.

17. The method of claim 16, wherein the geometric entity data defines, for a line representing an axis of a bullet of the tibial aimer, multiple poses of the line with respect to the unique fiducial, each of the poses of the line corresponding to a respective position of the aimer arm with respect to the handle.

18. The method of claim 17, wherein the geometric entity data defines a point representing a location of a tip of the aimer arm.

* * * * *